United States Patent [19]
Lawson et al.

[11] Patent Number: 5,354,758
[45] Date of Patent: Oct. 11, 1994

[54] BENZOMORPHANS USEFUL AS NMDA RECEPTOR ANTAGONISTS

[75] Inventors: John A. Lawson, Fremont, Calif.; Itsuo Uchida, Kanagawa, Japan

[73] Assignee: Japan Tobacco Inc., Tokyo, Japan

[21] Appl. No.: 991,365

[22] Filed: Dec. 16, 1992

[51] Int. Cl.$^5$ .................. C07D 221/26; A61K 31/445
[52] U.S. Cl. ........................................ 514/295; 546/97
[58] Field of Search ........................... 546/97; 514/295

[56] References Cited

U.S. PATENT DOCUMENTS

| | | |
|---|---|---|
| 3,382,249 | 5/1968 | Albertson . |
| 3,634,433 | 1/1972 | Moriyama et al. . |
| 4,108,857 | 8/1978 | Albertson . |
| 5,145,965 | 9/1992 | Allen et al. ........................... 546/97 |

FOREIGN PATENT DOCUMENTS 1185432  5/1968  United Kingdom .

OTHER PUBLICATIONS

Carroll et al., "Enantiomeric N-substituted N-normetazocines: a comparative study of affinities at σ, PCP, and μ opioid receptors" *J. Med. Chem.* (1992) 35:2812–2818.

Gill et al., "Systemic administration of MK-801 protects against ischemia-induced hippocampal neurodegeneration in the Gerbil" *J. Neurosci.* (1987) 7(10):3343–3349.

Goldberg et al., "Dextrorphan and dextromehtorphan attenuate hypoxic injury in neuronal culture" *Neurosci. Lett.* (1987) 80:11–15.

Hori et al., "Synthesis of some N-substituted 1,2,3,4,5,6-hexahydro-2,6-methzazocines (6,7-benzomorphans)" *Chem. Pharm. Bull.* (1985) 33(4):1707–1710.

McDonald et al., "MK-801 protects the neonatal brain from hypoxic-ischemic damage" *Eur. J. Pharmacol.* (1987) 140:359–361.

Meldrum, B., "Excitatory amino acid antagonists as potential therapeutic agents" *Neurotoxins and Their Pharmaceutical Implications*, Jenner, P., Ed., (1987) Raven Press, New York. pp. 33–53.

Rothman et al., "Ketamine protects hippocampal neurons from anoxia in vitro" *Neurosci.* (1987) 21(3):673–687.

*Primary Examiner*—Johann Richter
*Assistant Examiner*—John Peabody
*Attorney, Agent, or Firm*—Morrison & Foerster

[57] ABSTRACT

Compounds of the formula I

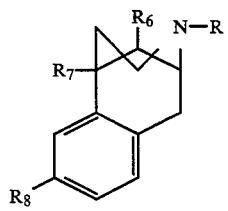

are disclosed. In this formula, R is a member selected from the group consisting of —CR$_1$R$_2$R$_3$, hydroxy, an alkoxy group having 1 to 4 carbon atoms and —NR$_4$R$_5$, in which at most one of R$_1$, R$_2$ and R$_3$ is hydrogen and the remainder are each independently selected from the group consisting of an alkyl group having 1 to 4 carbon atoms, an alkenyl group having 2 to 4 carbon atoms, an alkynyl group having 2 to 4 carbon atoms, a cycloalkyl group having 3 to 7 carbon atoms, a cycloalkylalkyl having 4 to 9 carbon atoms and a 3 to 6 membered cyclic ether; R$_4$ and R$_5$ are each independently hydrogen or an alkyl group having 1 to 4 carbon atoms; R$_6$ and R$_7$ are each independently hydrogen or an alkyl group having 1 to 4 carbon atoms; and R$_8$ is hydrogen, an alkyl group having 1 to 4 carbon atoms, hydroxy, an alkoxy group having 1 to 4 carbon atoms or halogen. Salts of these compounds are also disclosed. Also disclosed are pharmaceutical compositions of these compounds with a pharmaceutically acceptable carrier, the use of these materials as N-methyl-D-aspartate receptor antagonists, processes for preparing these compounds and salts, and methods to treat cerebral diseases by administering an effective amount of these compounds, salts or compositions.

15 Claims, 17 Drawing Sheets

Scheme 8

Scheme 11

Scheme 12

Scheme 13

Scheme 15

Scheme 16

Scheme 17

BENZOMORPHANS USEFUL AS NMDA RECEPTOR ANTAGONISTS

BACKGROUND OF THE INVENTION

1. Field of the Invention

The invention concerns a series of benzomorphan derivatives useful in the treatment of cerebrovascular disorders.

2. Background Information

Excessive excitation by neurotransmitters can cause the degeneration and death of neurons. It is believed that this excitotoxic action is mediated by the excitatory amino acids, glutamate and aspartate, acting at the N-methyl-D-aspartate (NMDA) receptor. This excitotoxic action is responsible for neuronal loss in cerebrovascular disorders such as cerebral ischemia or cerebral infarction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma.

The compounds of the invention, which are active as competitive antagonists of NMDA receptor-mediated ion-channel activation, are thus useful in the treatment of the above disorders. In addition, by this NMDA receptor antagonist action, the compounds of the invention are also useful for treating neurodegenerative disorders, spinal cord injury, and poisoning by exogenous NMDA poisons (for example, some forms of lathyrism). There are no specific therapies for these neurodegenerative disorders, but competitive and noncompetitive NMDA antagonists acting specifically to antagonize excitatory neurotransmission at NMDA receptors offer a novel therapeutic approach to these disorders; B. Meldrum in *Neurotoxins and Their Pharmacological Implications*, ed. P. Jenner, Raven Press, New York, 1987.

Recent reports in the literature have confirmed the protective action of certain NMDA antagonists in pharmacological models of neurodegenerative disorders (J. W. McDonald, F. S. Silverstein, and M. V. Johnston, *Eur. J. Pharmacol.*, (1987) 140: 359; R. Gill, A. C. Foster and G. N. Woodruff, *J. Neurosci.*, (1987) 7: 3343; S. M. Rothman, J. Thurston, R. E. Hauhart, G. D. Clark and J. S. Solomon, *Neurosci.*, (1987) 21: 673; M. P. Goldberg, P. C. Pham and D. W. Choi, *Neurosci. Let.*, (1987) 80: 11.

The present compounds have benzomorphan structures.

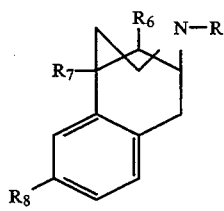

U.S. Pat. Nos. 4,108,857, 3,634,433 and 3,382,249, GB patent application No. 1185432, Japanese patent application JP A 52-3067 and *Chem. Pharm. Bull.* (1985, 33, 4, 1707–1710, Mikio Hori et al) disclose similar compounds as analgesic or anticonvulsant agents. *J. Med. Chem.* (1992, 35, 2812–2818, F. I. Carroll et al.) also disclose affinities of benzomorphan compounds for PCP, $\sigma$, and $\mu$ opioid receptors.

STATEMENT OF THE INVENTION

This invention relates to benzomorphan derivatives of the following General Formula I:

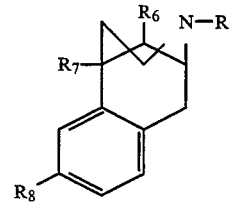

and the pharmaceutically acceptable salts thereof. In this formula:

R is a member selected from the group consisting of —$CR_1R_2R_3$, hydroxy, an alkoxy group having from 1 to 4 carbon atoms and —$NR_4R_5$, in which at most one of $R_1$, $R_2$ and $R_3$ is hydrogen and the remainder are each independently selected from the group consisting of an alkyl group having from 1 to 4 carbon atoms, an alkenyl group having from 2 to 4 carbon atoms, an alkynyl group having from 2 to 4 carbon atoms, a cycloalkyl group having from 3 to 7 carbon atoms, a cycloalkylalkyl group having from 4 to 9 carbon atoms and a 3 to 6 membered cyclic ether;

$R_4$ and $R_5$ are each independently hydrogen or an alkyl group having 1 to 4 carbon atoms;

$R_6$ and $R_7$ are each independently hydrogen or an alkyl group having 1 to 4 carbon atoms; and $R_8$ is hydrogen, an alkyl group having 1 to 4 carbon atoms, hydroxy, an alkoxy group having 1 to 4 carbon atoms or halogen;

subject to the proviso that when $R_6$, $R_7$ and $R_8$ are methyl, methyl and hydroxy respectively, R is not

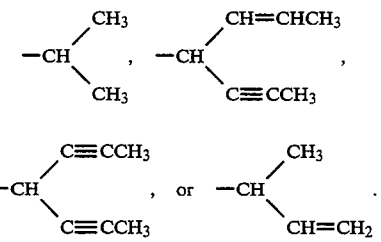

In another aspect this invention provides pharmaceutical compositions made up of one or more of these compounds with pharmaceutically acceptable carriers. These compositions are useful as N-methyl-D-aspartate receptor antagonists. In other aspects, this invention provides processes for preparing these compounds, and methods to treat cerebral diseases by administering to a patient an effective amount of these pharmaceutical compositions.

DETAILED DESCRIPTION OF THE INVENTION

BRIEF DESCRIPTION OF THE DRAWINGS

This invention will be described with reference being made to the drawings in which.

DESCRIPTION OF PREFERRED EMBODIMENTS

Figure 1:
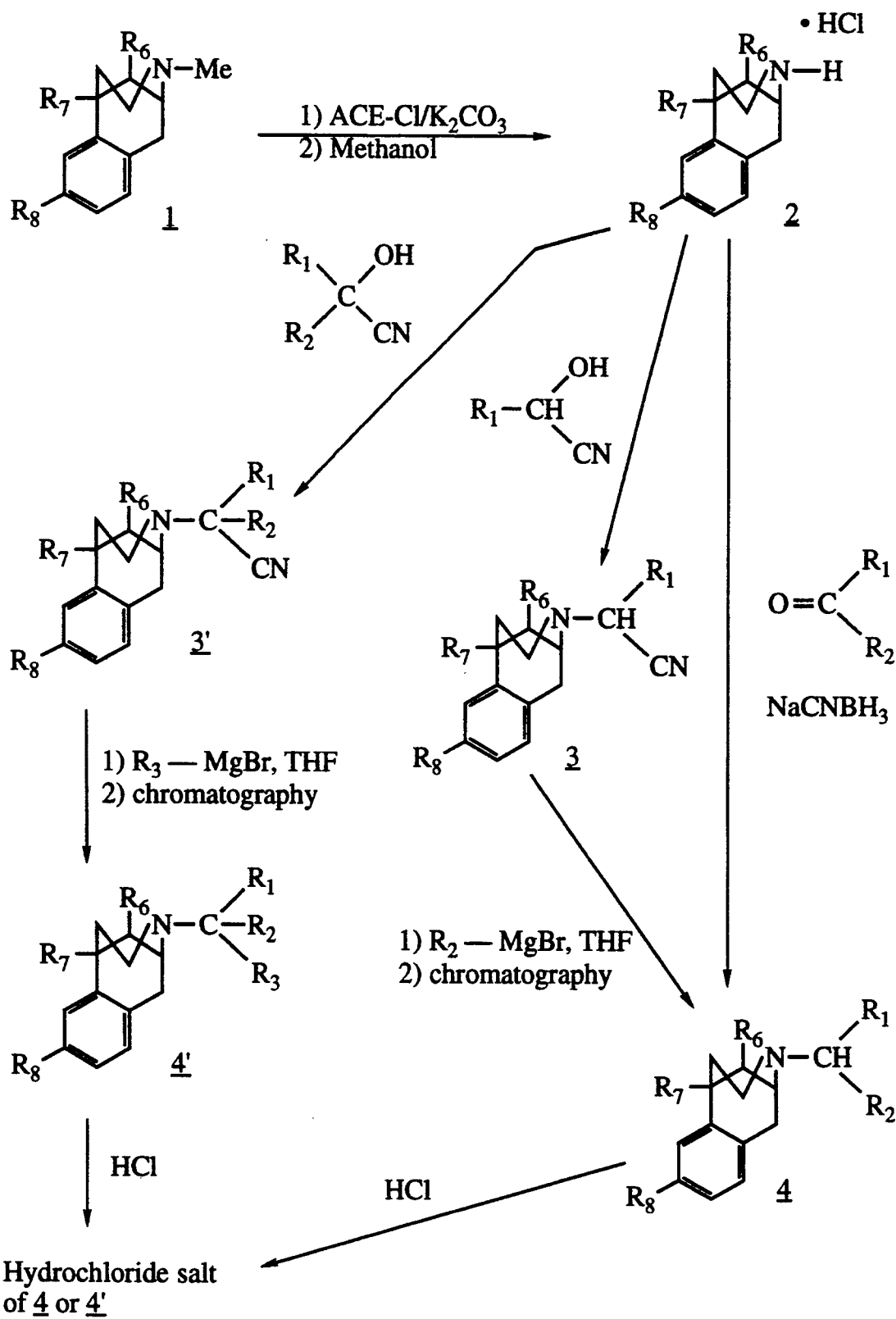
FIG. 1 is a general depiction of an overall scheme of chemical reactions which can be used to prepare compounds of the invention with —CR$_1$R$_2$R$_3$ as N-substituent.

The present invention provides compounds and pharmaceutical compositions based on them which are useful as N-methyl-D-aspartate receptor antagonists and in the treatment of cerebral diseases such as cerebral ischemia, cerebral hypoglycemia, epilepsy, anxiety and convulsion.

THE COMPOUNDS

The compounds of this invention are benzomorphan derivatives of the following General Formula I:

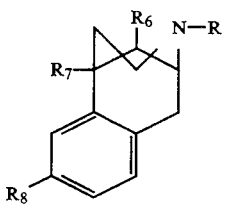

or a pharmaceutically acceptable salt thereof. In this formula:

R is a member selected from the group consisting of —CR$_1$R$_2$R$_3$, hydroxy, an alkoxy group having from 1 to 4 carbon atoms and —NR$_4$R$_5$, in which at most one of R$_1$, R$_2$ and R$_3$ is hydrogen and the remainder are each independently selected from the group consisting of an alkyl group having from 1 to 4 carbon atoms, an alkenyl group having from 2 to 4 carbon atoms, an alkynyl group having from 2 to 4 carbon atoms, a cycloalkyl group having from 3 to 7 carbon atoms, a cycloalkylalkyl group having from 4 to 9 carbon atoms and a 3 to 6 membered cyclic ether;

R$_4$ and R$_5$ are each independently hydrogen or an alkyl group having 1 to 4 carbon atoms;

R$_6$ and R$_7$ are each independently hydrogen or an alkyl group having 1 to 4 carbon atoms; and R$_8$ is hydrogen, an alkyl group having 1 to 4 carbon atoms, hydroxy, an alkoxy group having 1 to 4 carbon atoms or halogen;

subject to the proviso that when R$_6$, R$_7$ and R$_8$ are methyl, methyl and hydroxy respectively, R is not

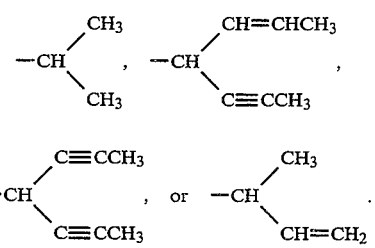

As used herein the term "an alkyl group having 1 to 4 carbon atoms" is defined to include straight or branched chain alkyl groups having from 1 to 4 carbon atoms. These include —CH$_3$, —CH$_2$CH$_3$, —(CH$_2$)$_2$CH$_3$, —CH(CH$_3$)$_2$, —(CH$_2$)$_3$CH$_3$, —CH$_2$CH(CH$_3$)$_2$, —CH(CH$_3$)CH$_2$CH$_3$, and —C(CH$_3$)$_3$. The term "an alkenyl group having 2 to 4 carbon atoms" is defined to include straight or branched chain alkenyl groups having from 2 to 4 carbon atoms with 1 or 2 olefin unsaturations. These include, for example, —CH=CH$_2$, —CH=CHCH$_3$, —CH$_2$CH=CH$_2$, —C(CH$_3$)=CH$_2$, —CH=CHCH$_2$CH$_3$, —CH$_2$CH=CHCH$_3$, —(CH$_2$)$_2$CH=CH$_2$, —CH=C(CH$_3$)$_2$, CH$_2$C(CH$_3$)=CH$_2$, —C(CH$_3$)=CHCH$_3$, —CH(CH$_3$)CH=CH$_2$, —C(=CH$_2$)CH$_2$CH$_3$, —CH=CHCH=CH$_2$ and —C(=CH$_2$)CH=CH$_2$. The term "an alkynyl group having 2 to 4 carbon atoms" is defined to include straight or branched chain alkynyl groups having from 2 to 4 carbon atoms with 1 or 2 acetylenic unsaturations and up to 1 olefinic unsaturation. These include, for example, —C≡CH, —C≡CCH$_3$, —CH$_2$C≡CH, —C≡CCH$_2$CH$_3$, —CH$_2$C≡CCH$_3$, —(CH$_2$)$_2$C≡CH, —C(CH$_3$)C≡CH, —C≡C—C≡CH, —C≡CCH=CH$_2$, —CH=CHC≡CH and —C(=CH$_2$)C≡CH. The term "a cycloalkyl group having 3 to 7 carbon atoms" includes cyclopropyl, cyclobutyl, cyclopentyl, cyclohexyl and cycloheptyl. The term "a cycloalkylalkyl group having 4 to 9 carbon atoms" includes groups such as, for example, cyclopropylmethyl, cyclopropylethyl, cyclopropylpropyl, cyclopropylbutyl, cyclopropylpentyl, cyclopropylhexyl, cyclobutylmethyl, cyclobutylethyl, cyclobutylpropyl, cyclobutylbutyl, cyclobutylpentyl, cyclopentylmethyl, cyclopentylethyl, cyclopentylpropyl, cyclopentylbutyl, cyclohexylmethyl, cyclohexylethyl, cyclohexylpropyl, cycloheptylmethyl, cycloheptylethyl, and the like. The term "a 3- to 6-membered cyclic ether" includes groups having 2 to 5 cyclic carbons and a cyclic ether oxygen. Such groups include, for example,

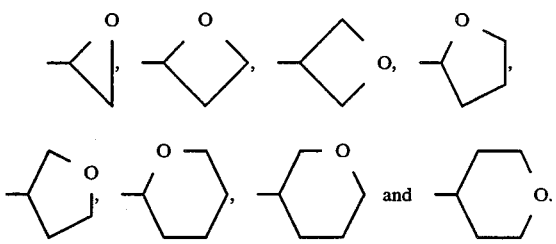

The term "an alkoxy group having 1 to 4 carbon atoms" is defined to include groups such as methoxy, ethoxy, propoxy, iso-propoxy, butoxy, iso-butoxy, sec-butoxy, tert-butoxy. The term "halogen" is defined to include the fluorine, chlorine, bromine and iodine organic substituent groups.

In preferred compounds, R is —$CR_1R_2R_3$, an alkoxy group having 1 to 4 carbon atoms or —$NR_4R_5$ in which at most one of $R_1$, $R_2$ and $R_3$ is hydrogen and the remainder of $R_1$, $R_2$ and $R_3$ are each independently an alkyl group having 1 to 4 carbon atoms, an alkenyl group having 2 to 4 carbon atoms, an alkynyl group having 2 to 4 carbon atoms, a cycloalkyl group having 3 to 7 carbon atoms, a cycloalkylalkyl having 4 to 9 carbon atoms or a 3 to 6 membered cyclic ether; $R_4$ and $R_5$ are each independently hydrogen or an alkyl group having 1 to 4 carbon atoms; $R_6$ and $R_7$ are each independently an alkyl group having 1 to 4 carbon atoms, and $R_8$ is hydrogen, hydroxy, an alkoxy group having 1 to 4 carbon atoms or halogen.

In more preferred compounds, R is —$CR_1R_2R_3$, methoxy, ethoxy, propoxy, or —$NR_4R_5$ in which at most one of $R_1$, $R_2$ and $R_3$ is hydrogen, and the remainder of $R_1$, $R_2$ and $R_3$ are each independently methyl, ethyl, propyl, ethenyl, propenyl, ethynyl, propynyl, cyclopropyl, cyclobutyl, cyclopropylmethyl, cyclopropylethyl, cyclobutylmethyl, cyclobutylethyl,

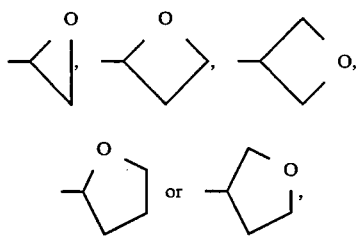

$R_4$ and $R_5$ are each independently hydrogen, methyl, ethyl, propyl; $R_6$ and $R_7$ are each independently methyl, or ethyl and $R_8$ is hydrogen, methyl, hydroxy, methoxy, chlorine or fluorine.

PHARMACEUTICALLY ACCEPTABLE SALTS

These compounds can exist as salts. The tertiary amine group present in the compounds of the invention can form acid-addition salts of pharmaceutically acceptable inorganic or organic acids, such as of strong mineral acids, for example, hydrohalic, hydrochloric or hydrobromic acid; sulfuric, phosphoric or nitric acid; aliphatic or aromatic carboxylic or sulfonic acids, for example, acetic, propionic, succinic, glycolic, lactic, malic, tartaric, gluconic, citric, ascorbic, maleic, fumaric, pyruvic, palmoic, nicotinic, methanesulfonic, ethanesulfonic, hydroxyethanesulfonic, benzenesulfonic, p-toluenesulfonic or naphthalenesulfonic acid.

ISOMERS, ETC.

The compounds of the invention contain at least two asymmetric carbon atoms. The invention includes individual enantiomers, diastereomers, or mixtures thereof, which may be prepared or isolated by methods known in the art. The invention includes individual (+)-and (−)- optical isomers derived from the benzomorphan skeleton and mixtures thereof, which may be prepared or isolated by the methods known in the art. Usually the (+)-isomers are more active with less side effects. For this reason they are preferred. A material is considered to be "substantially isomerically pure" (such as optically and geometrically pure) when it contains at least about 75% and preferably 85% or especially at least about 90% isomerical purity.

PHARMACEUTICAL FORMULATIONS

The compounds of the invention have pharmacological advantages which render them useful for treating cerebrovascular diseases. In this application one or a mixture of two or more of these compounds may be administered according to any convenient or effective methods for introducing foreign substances into the blood stream of mammals, such as by oral, rectal, nasal, buccal, vaginal, or parenteral routes. The effective dosage level is, for example, 0.01 to 100 mg/kg, preferably about 0.05 to 50 mg/kg. Doses of this size may be administered on a regimen of 1 to 4 times per day. The pharmaceutical formulations comprising the compounds of the invention may be in dosage forms such as tablets, pills, capsules, powders, or granules for oral administration.

Compounds here provided can be formulated into pharmaceutical compositions by admixture with pharmaceutically acceptable nontoxic carriers. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well known in the pharmaceutical art, for example as described in *Remington's Pharmaceutical Sciences*, Mack Publishing Company, Easton, Pa. 1975, incorporated by reference. Formulations for parenteral administration may contain as common excipients, sterile water or saline, polyalkylene glycols such as polyethylene glycol, oils of vegetable origin, hydrogenated naphthalenes and the like. Formulations for vaginal or rectal administration, e.g., suppositories, may contain as excipients, for example, polyalkylene glycols, petroleum jelly, cocoa butter, and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

For oral administration, a pharmaceutically acceptable nontoxic composition can be formed by the incorporation of any of the normally employed excipients, oral dose extenders or carriers such as, for example, pharmaceutical grades of mannitol, lactose, starch, magnesium stearate, sodium saccharin, talcum, cellulose, glucose, sucrose, magnesium, carbonate, and the like. Such compositions can take the form of solutions, suspensions, tablets, pills, capsules, powders, sustained-release formulations, and the like. Such compositions may contain 0.1–95% active ingredient, preferably 1–70%, with the remainder being carrier.

The materials of this invention can be employed as the sole active agent in a pharmaceutical composition or can be used in combination with other active ingredients.

The effects of the compounds of the invention can be evaluated in in vitro tests or in vivo animal tests using mammals such as mice, rats, rabbits, dogs and monkeys, or tissues or enzyme preparations thereof.

Competition binding for NMDA receptor with radiolabeled known NMDA antagonist is one convenient way to ascertain the ability of the compounds of the invention to bind to target cerebral cells. This evaluation can be made according to the method of J. Lehman et al., 1988. In addition, the ability to antagonize NMDA receptors can be evaluated according to the method of Ferkany et al., 1988.

PREPARATION OF THE COMPOUNDS

The compounds of this invention are new materials. As such they can not be purchased and must be prepared.

An overall synthetic route to compounds with —$CR_1R_2R_3$ as N-substituent is shown generically in Scheme 1 presented as FIG. 1.

As shown in Scheme 1, the synthesis begins with a known tricyclic compound 1. This material should be resolved into its desired stereoisomers if a stereoisomerically pure product is sought. This starting material is available as metazocine ($R_6$=Me, $R_7$=Me and $R_8$=OH) or its $R_6R_7R_8$-substituted analogs. The material is resolved as needed and reacted with ACE-Cl(α-chloroethylchloroformate)/$K_2CO_3$, typically at reflux for 12 to 24 hours, followed by reaction with methanol at reflux to effect demethylation and afford product 2.

Intermediate 2 can be converted directly to the desired product 4 by adding an $R_1R_2C$=O (ketone) in the presence of a sodium cyanoborohydride ($NaCNBH_3$), and the like at 50° to 100° C.

In the other route, intermediate 2 is reacted with a cyanohydrin, $R_1$—CH(OH)CN or $R_1R_2$—C(OH)CN to afford product 3 or 3' respectively. Thereafter, the intermediate 3 or 3' can be converted to the desired product 4 or 4' respectively via Grignard reaction by adding $R_2$—MgBr or $R_3$13 MgBr in tetrahydrofuran (THF).

Acidification with hydrochloric acid in ether and filtration afforded the corresponding hydrochloride salts of the product 4 or 4'.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, and under atmospheric or super-atmospheric pressure. The preferred solvents, catalysts and reaction conditions are set forth in the appended illustrative examples. The invention further includes any variant of the present processes, in which an intermediate product obtainable at any stage thereof is used as starting material and the remaining steps are carried out, or the process is discontinued at any stage thereof, or in which the starting materials are formed under the reaction conditions, or in which the reaction components are used in the form of their salts or optically pure antipodes.

The following examples and illustrations are intended to illustrate the invention and are not to be construed as being limitations thereon.

Figure 2:
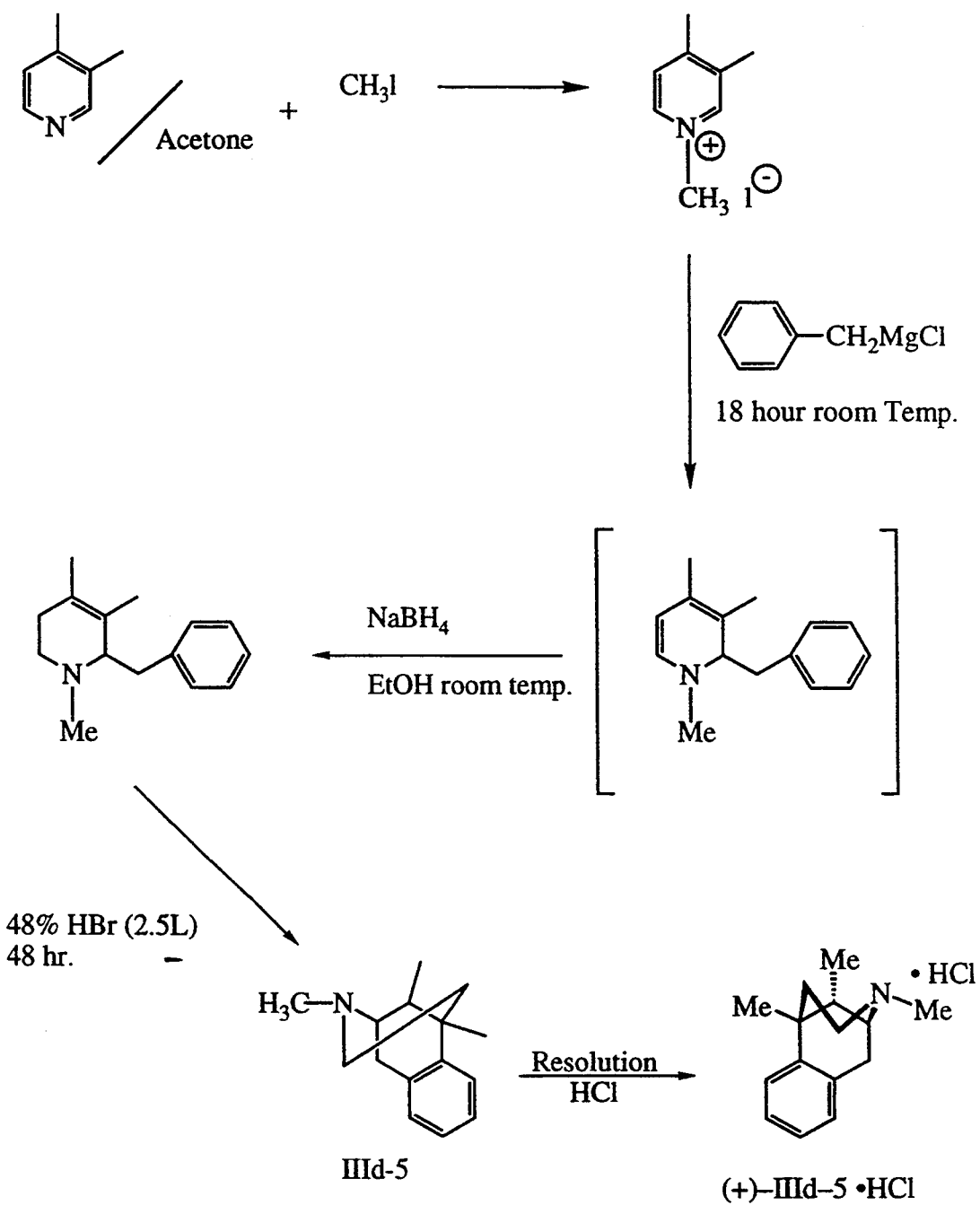
FIG. 2 is a depiction of the chemical reactions employed in Example 1.
Figure 3:
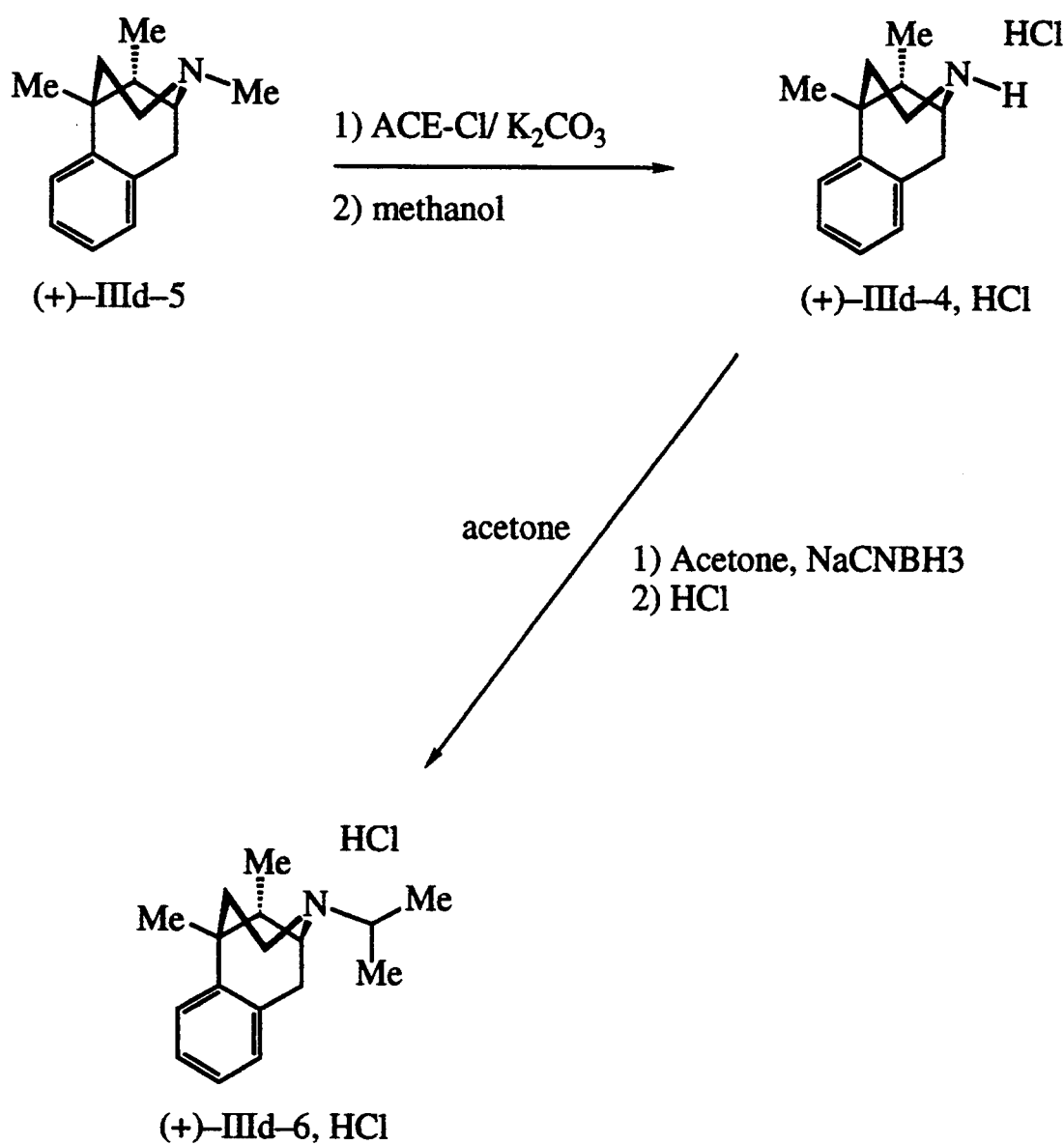
FIG. 3 is a depiction of the chemical reactions employed in Examples 2 and 3.
Figure 4:
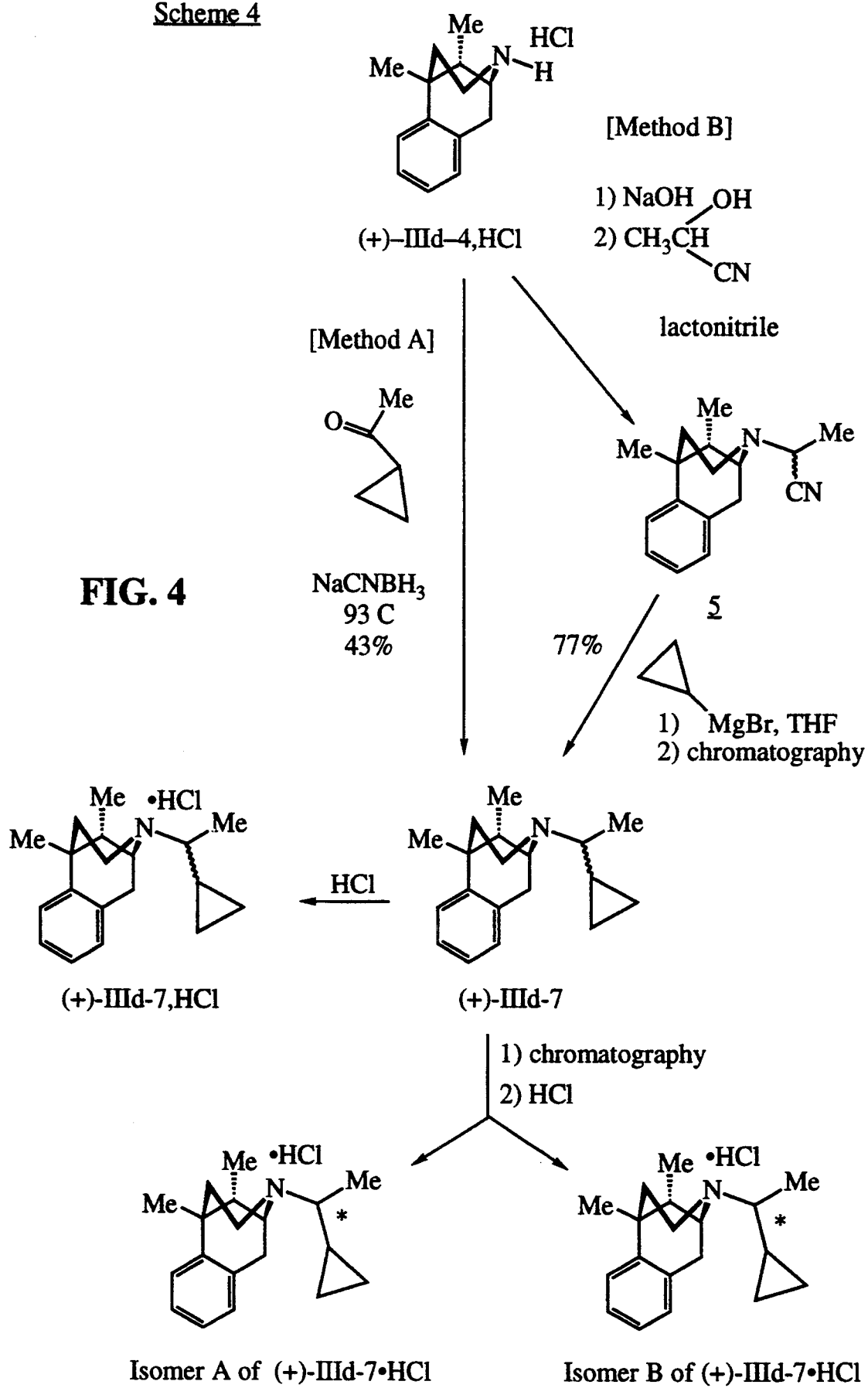
FIG. 4 is a depiction of the chemical reactions employed in Example 4.
Figure 5:
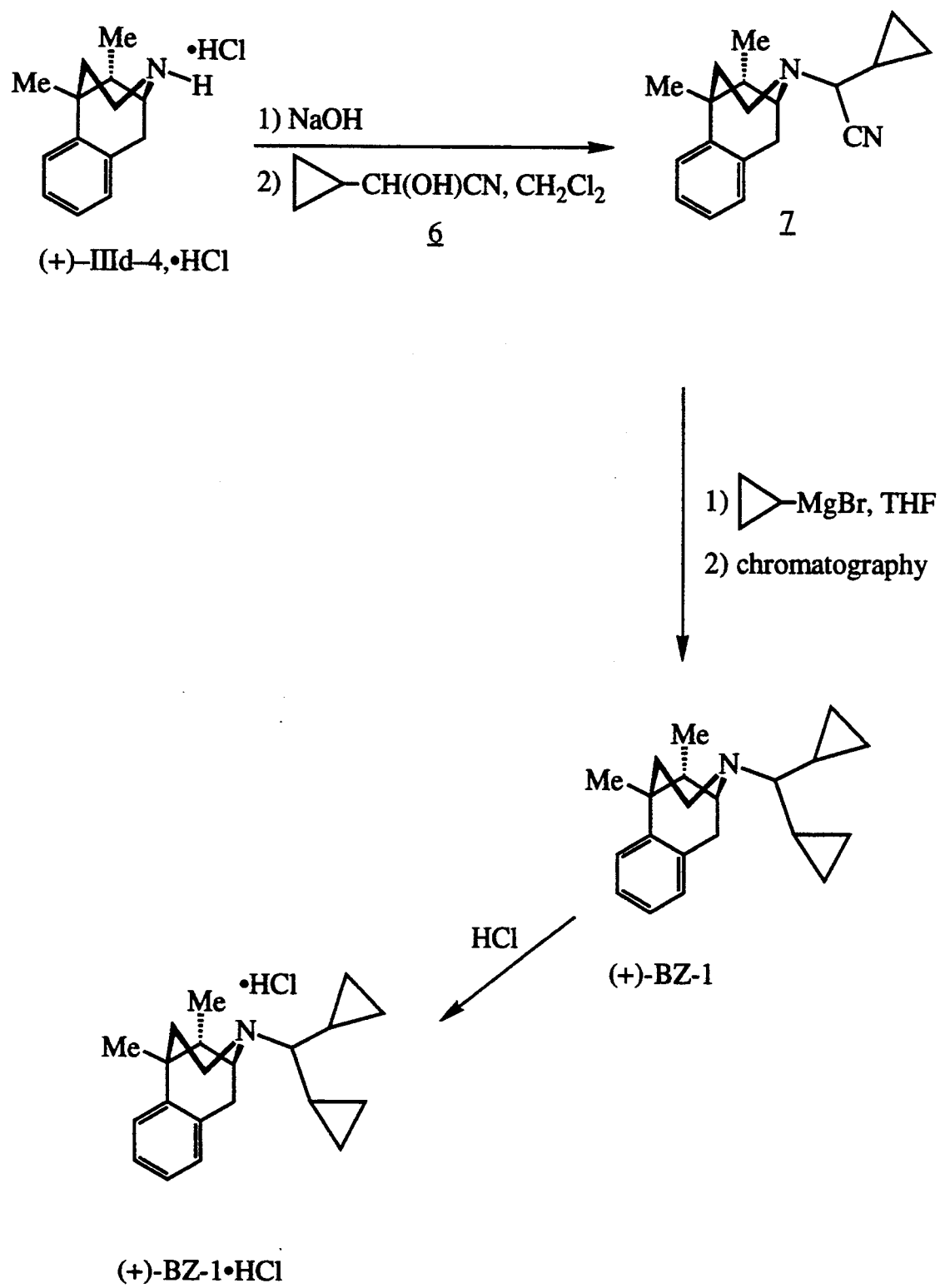
FIG. 5 is a depiction of the chemical reactions employed in Example 5.
Figure 6:
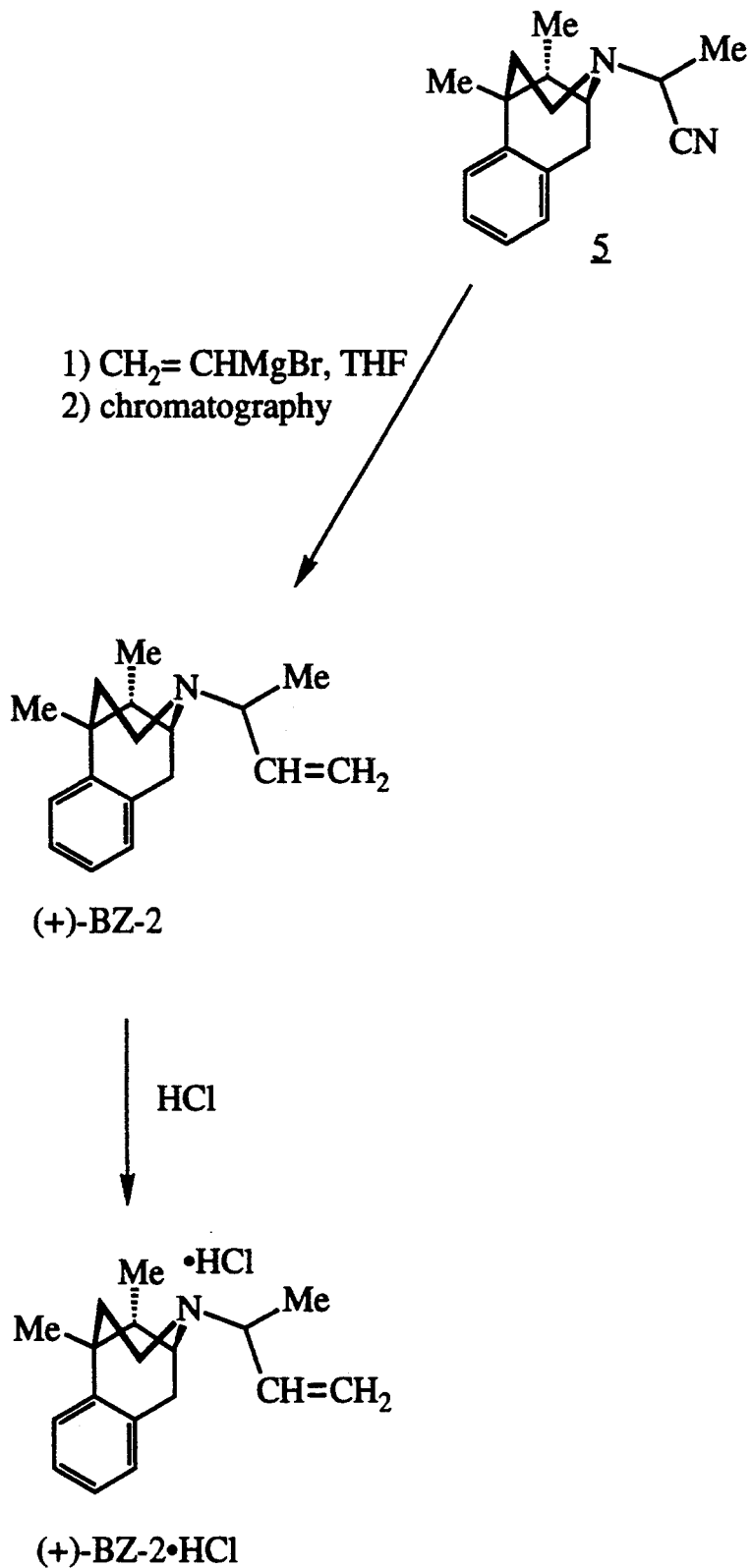
FIG. 6 is a depiction of the chemical reactions employed in Example 6.
Figure 7:
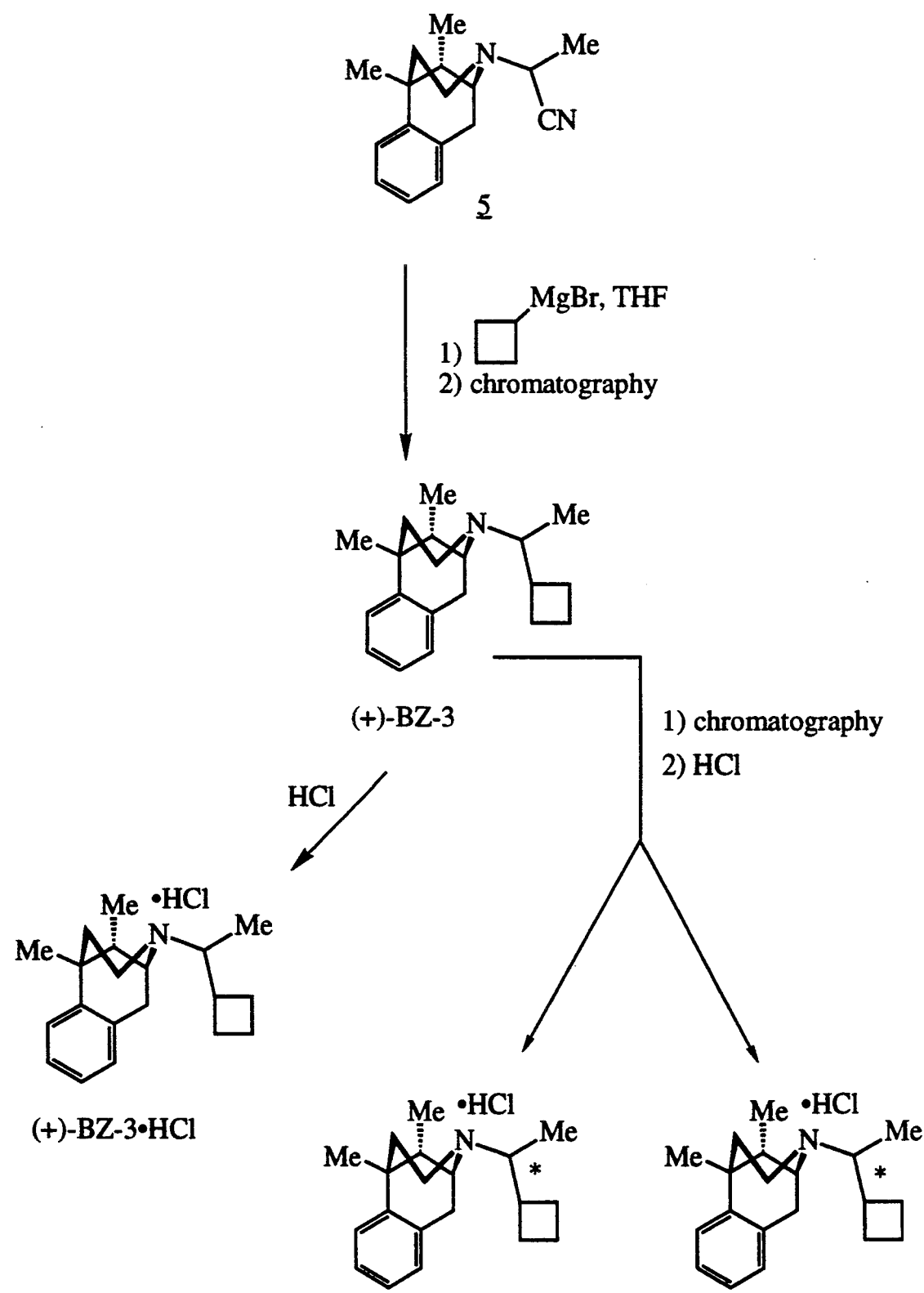
FIG. 7 is a depiction of the chemical reactions employed in Example 7.
Figure 8:
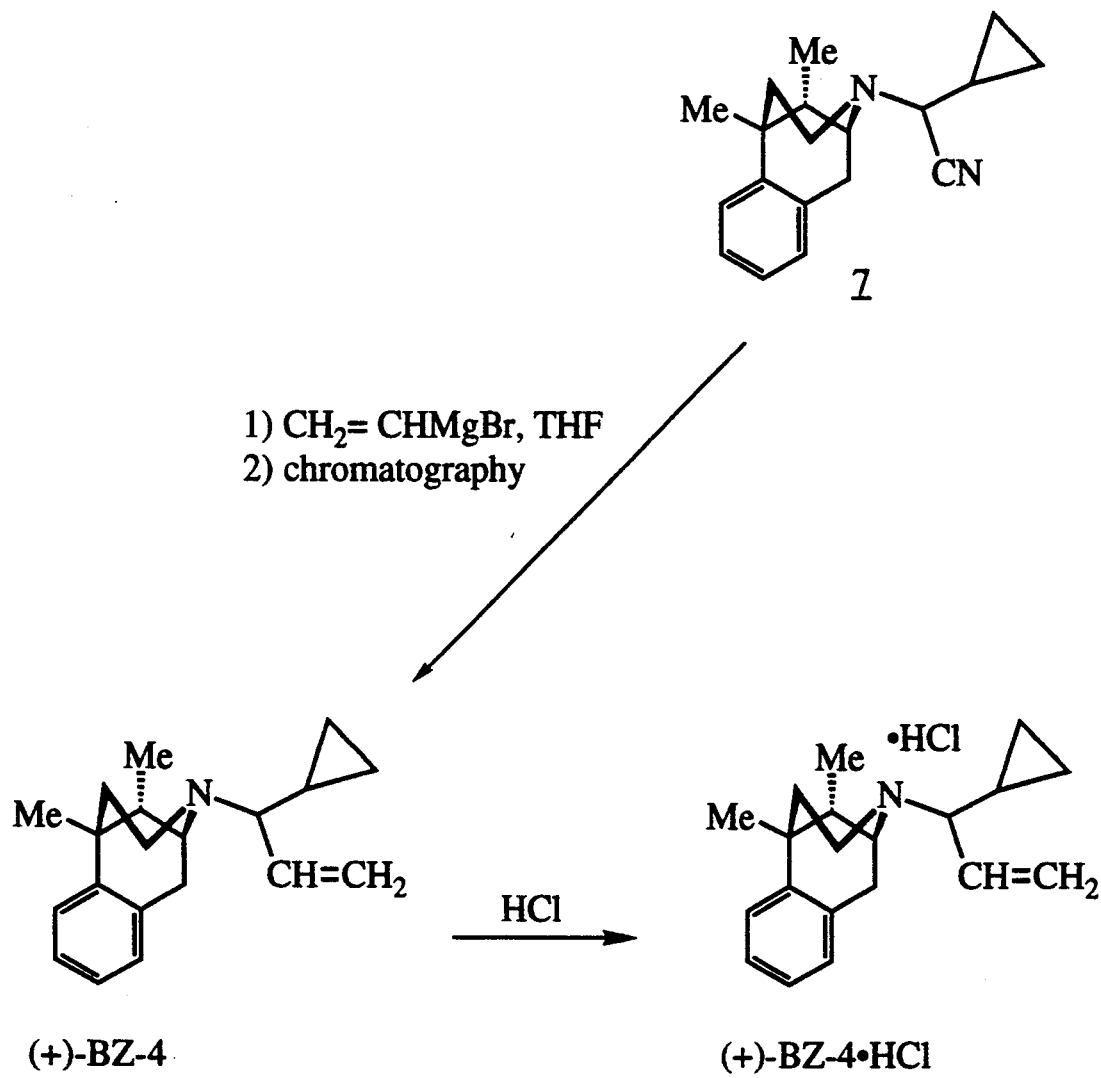
FIG. 8 is a depiction of the chemical reactions employed in Example 8.
Figure 9:
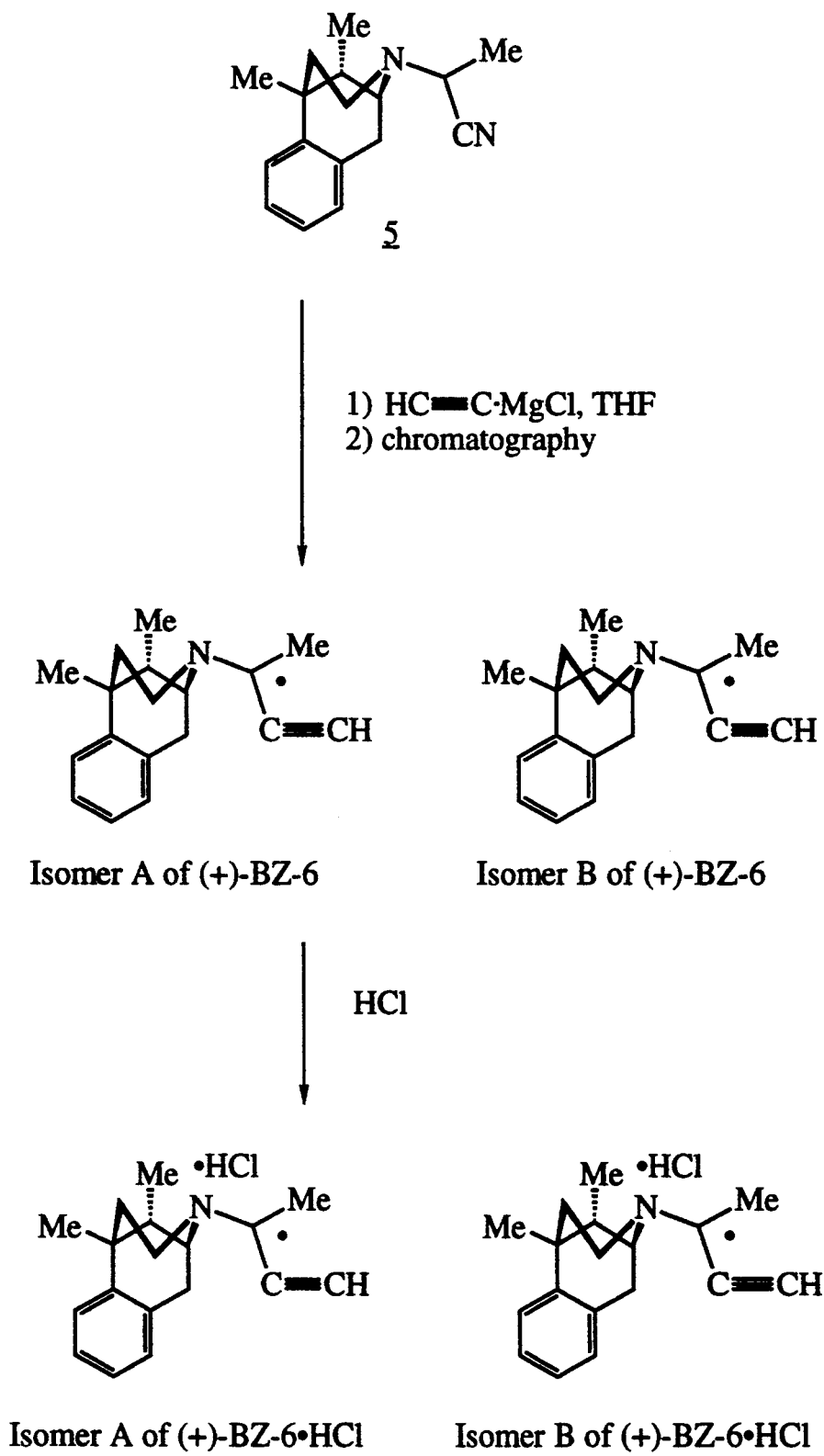
FIG. 9 is a depiction of the chemical reactions employed in Example 9.
Figure 10:
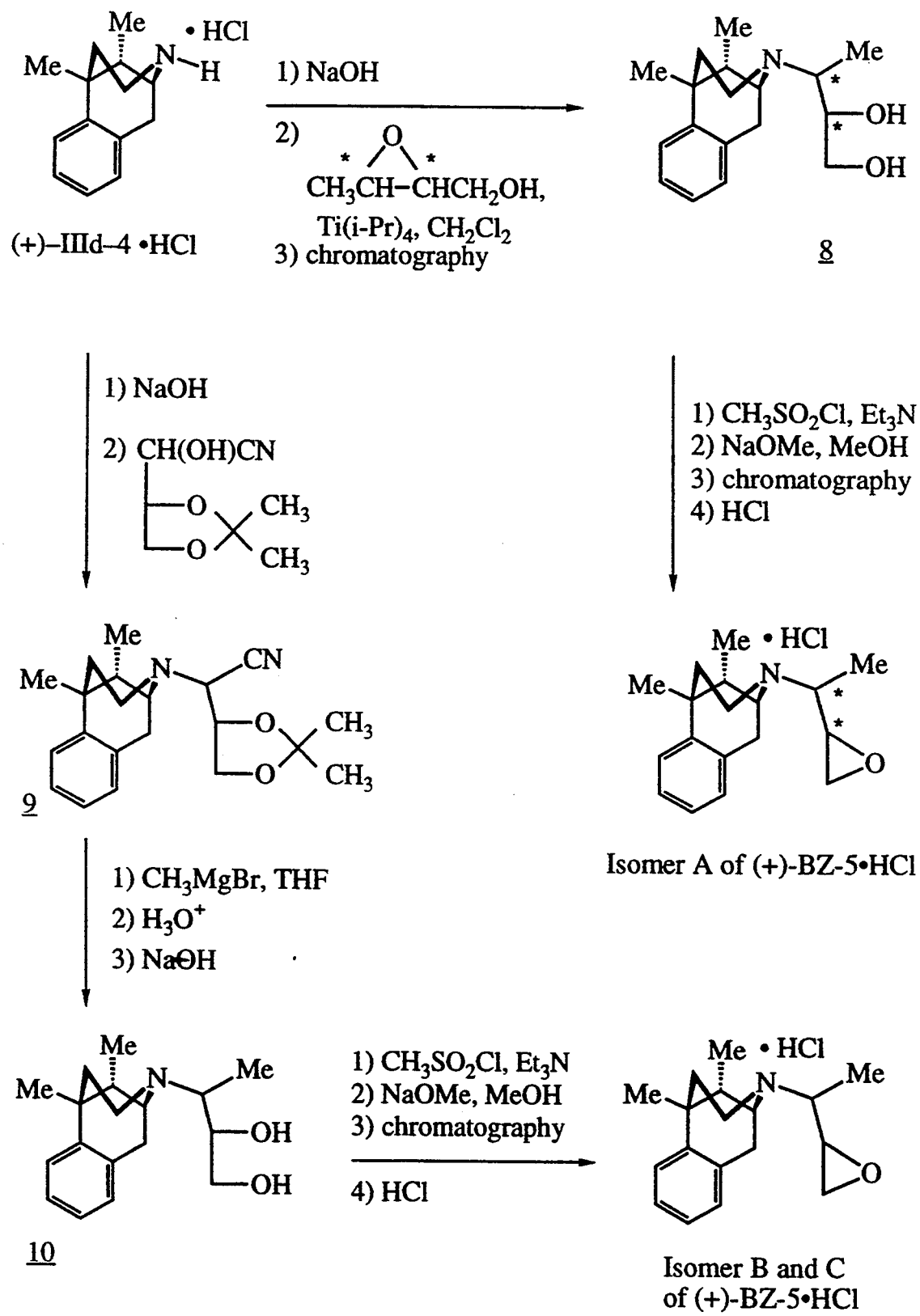
FIG. 10 is a depiction of the chemical reactions employed in Example 10.
Figure 11:
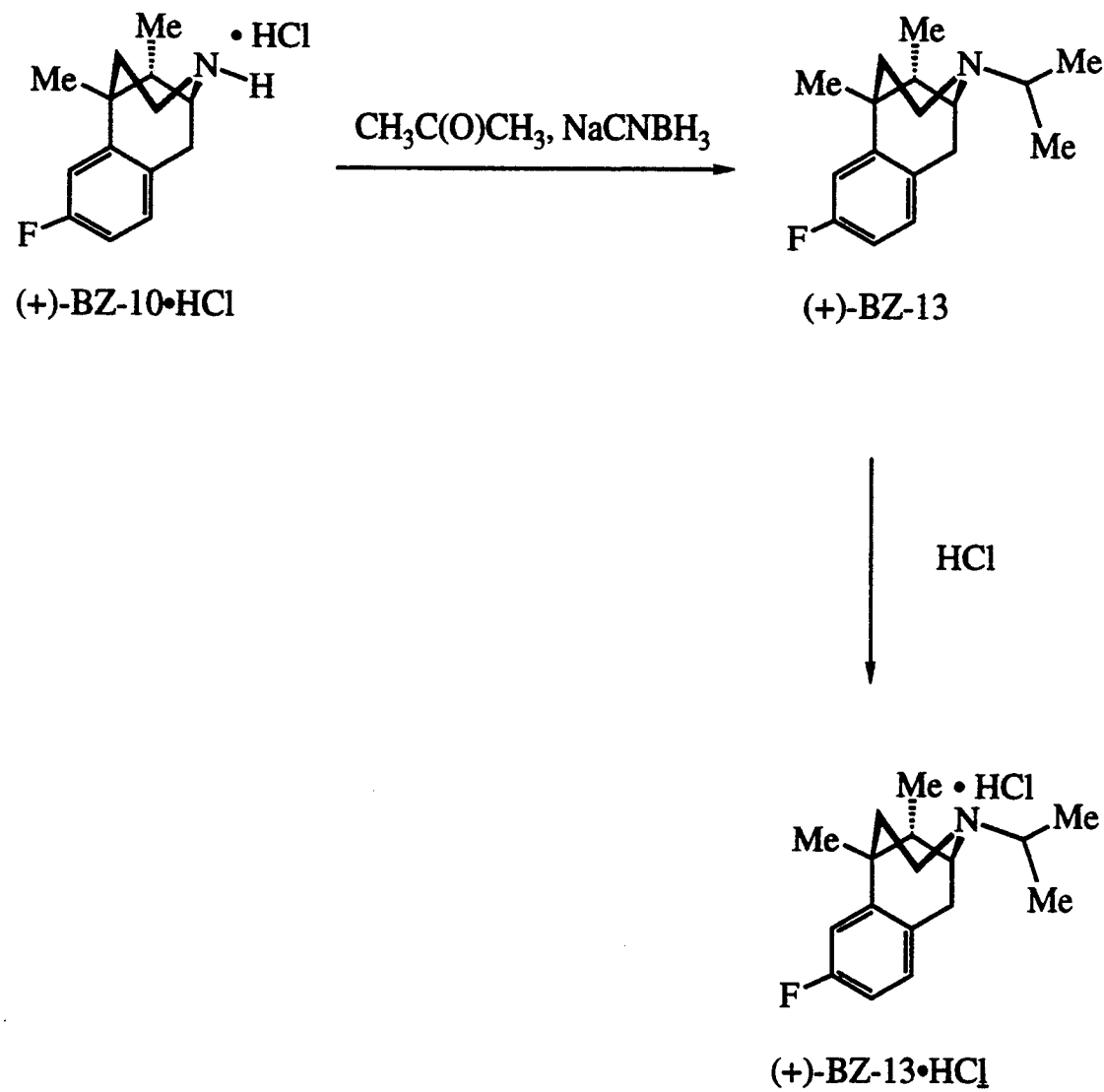
FIG. 11 is a depiction of the chemical reactions employed in Example 11.
Figure 12:
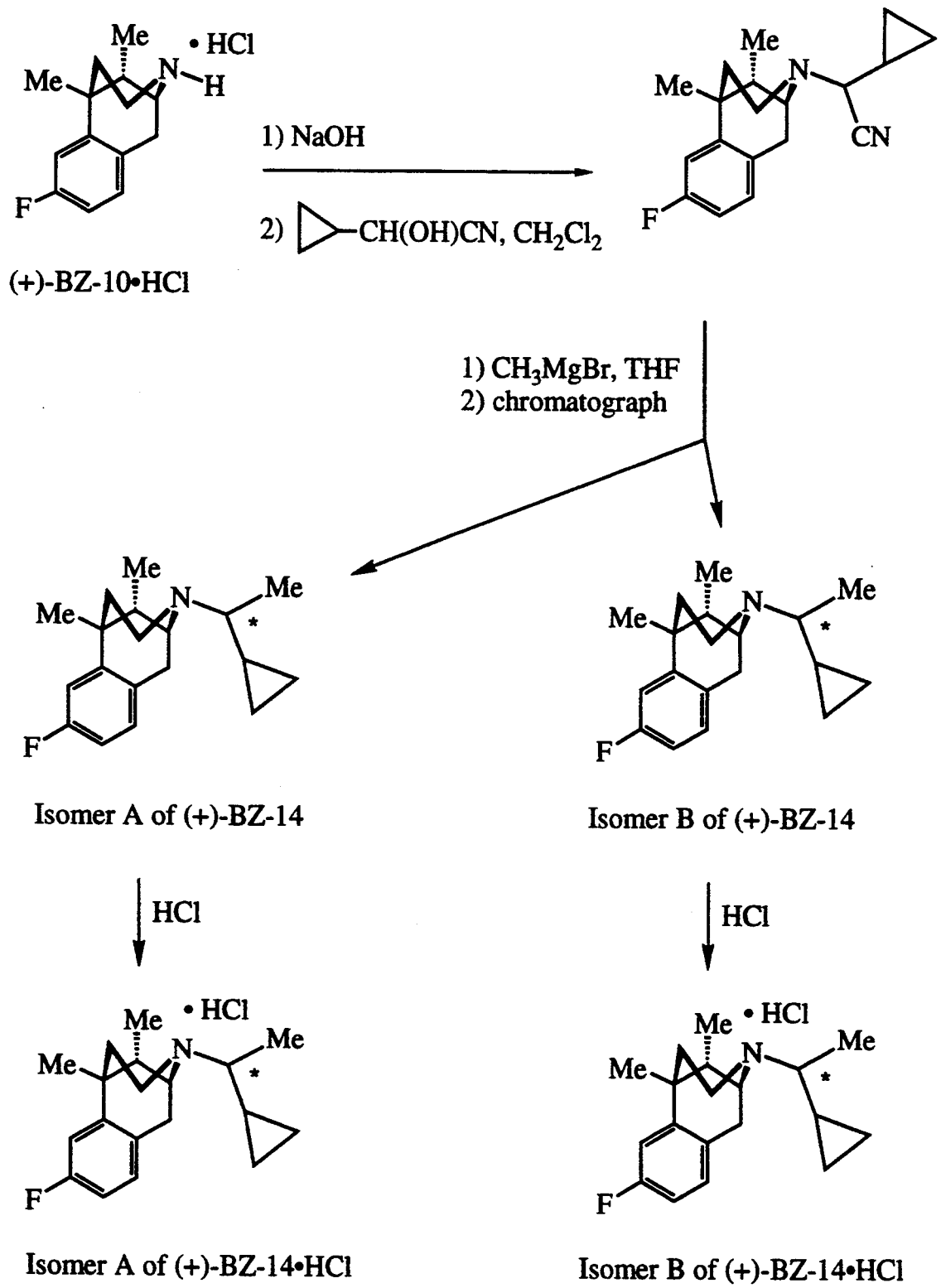
FIG. 12 is a depiction of the chemical reactions employed in Example 12.
Figure 13:
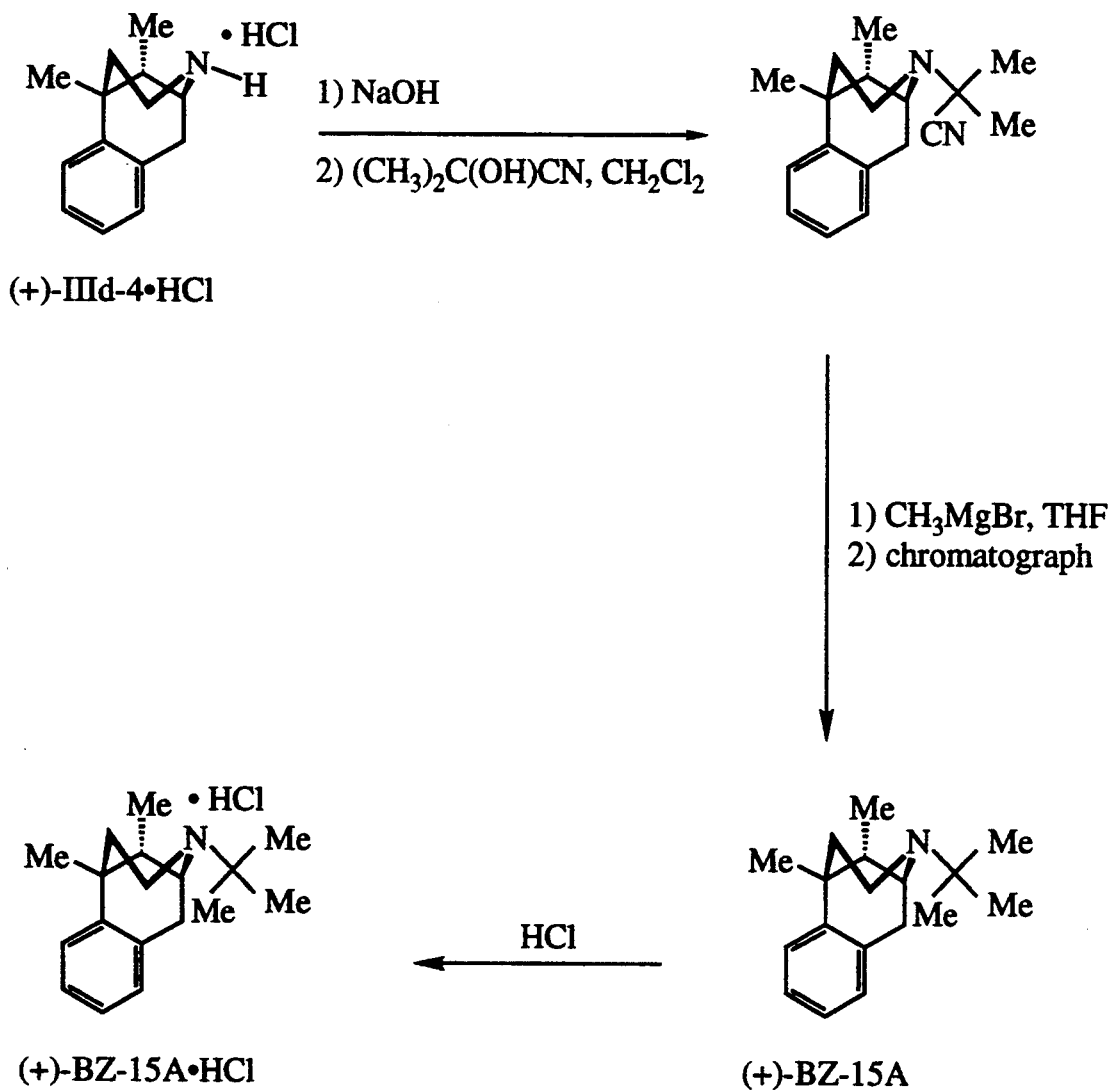
FIG. 13 is a depiction of the chemical reactions employed in Example 13.
Figure 14:
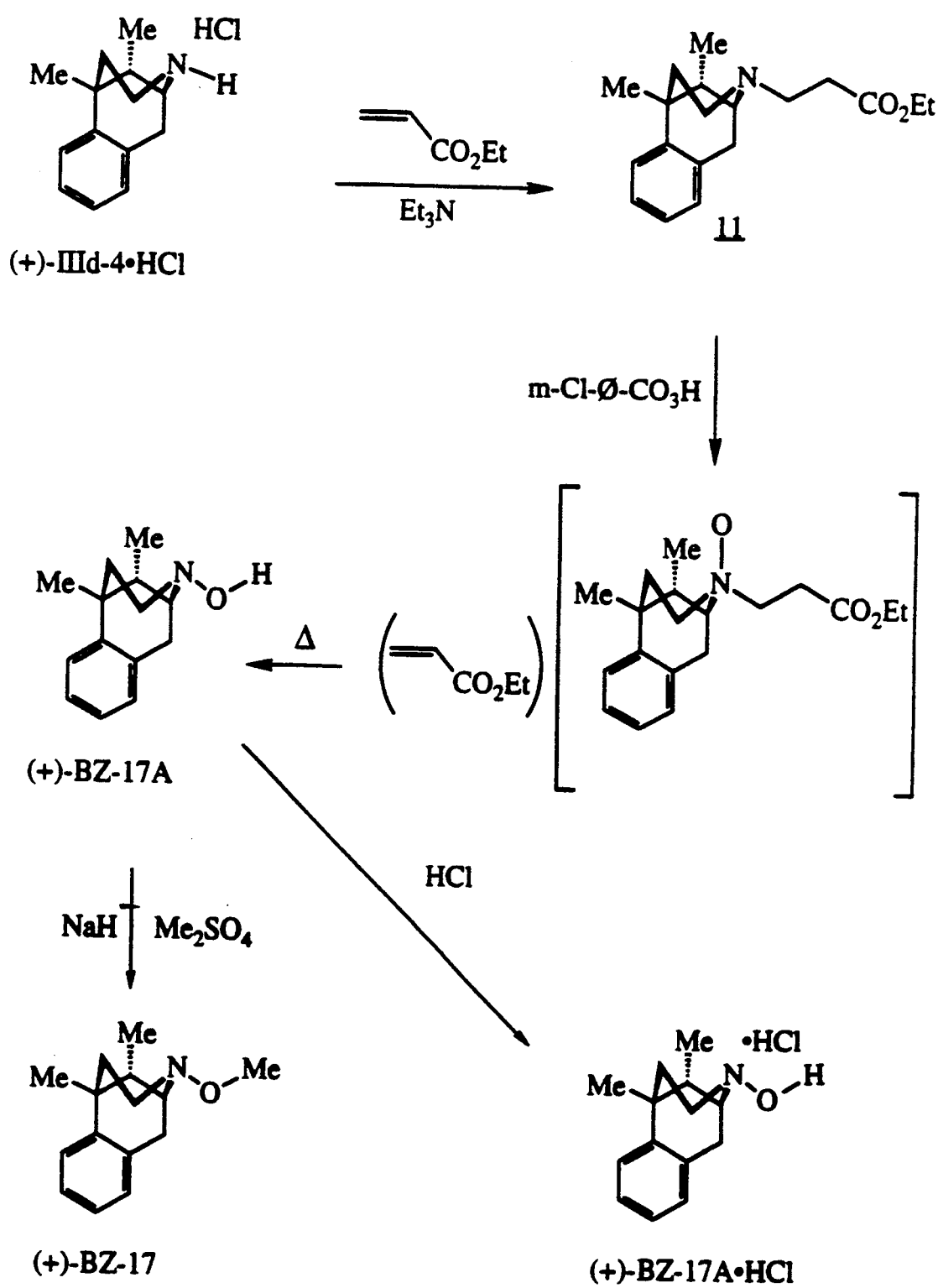
FIG. 14 is a depiction of the chemical reactions employed in Example 14.
Figure 15:
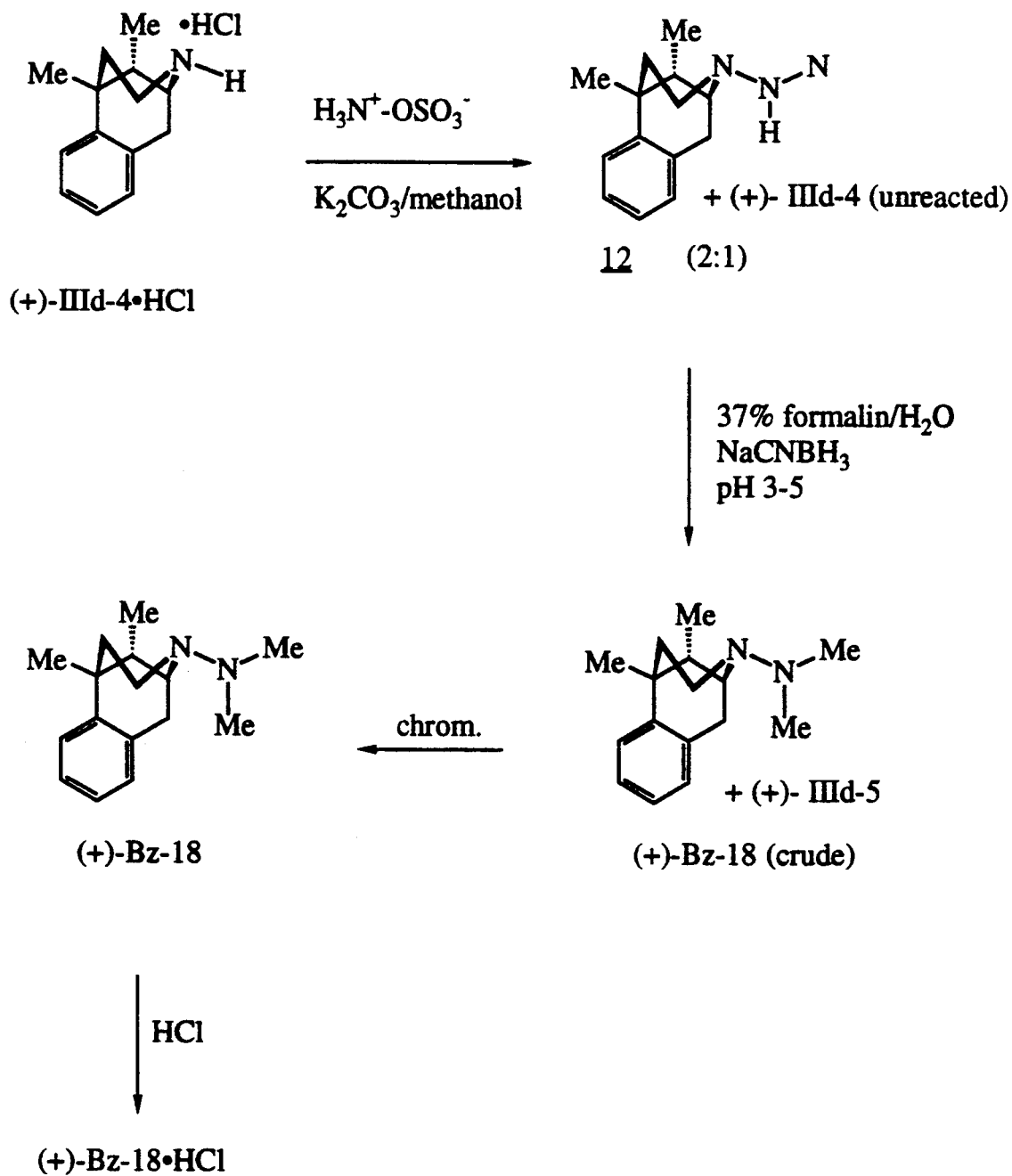
FIG. 15 is a depiction of the chemical reactions employed in Example 15.
Figure 16:
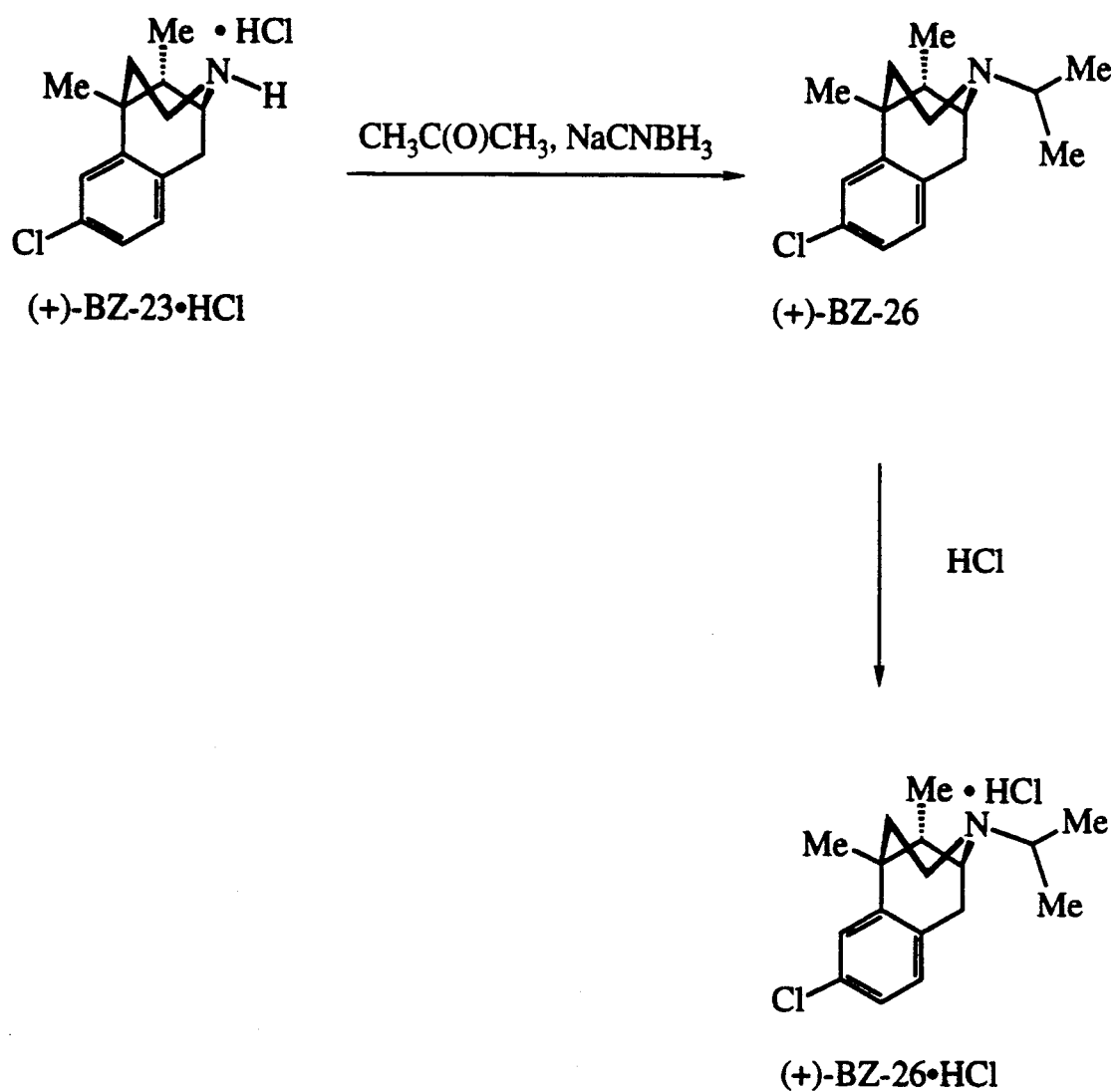
FIG. 16 is a depiction of the chemical reactions employed in Example 16.

Reaction Scheme 2 (FIG. 2) corresponds to Example 1,

Reaction Scheme 3 (FIG. 3) corresponds to Examples 2 and 3, and

Reaction Schemes 4–17 (FIGS. 4–17) correspond to Examples 4–17 respectively.

EXAMPLES

Example 1

Synthesis of 2,5,9-trimethyl-6,7-benzomorphan ((±)-IIId-5

As shown in Scheme 2 (in FIG. 2), a solution of 100 g of 3,4-dimethylpyridine in 800 ml of acetone was added dropwise to 57.27 mL of methyl iodide. The reaction mixture was stirred at room temperature for 18 hrs. The solid was collected by filtration and washed with cold ether. After drying under vacuum, there was obtained 202 g of 1,3,4-trimethylpyridinium iodide. The subsequent Grignard reaction was conducted under standard conditions to afford an unstable intermediate that was utilized immediately.

To a solution of 3.02M of benzylmagnesium chloride (2M solution) in THF was added portionwise 300 g (20 g portions) of 1,3,4-trimethylpyridinium iodide. The reaction mixture was stirred at room temperature for 18 hrs. The THF was evaporated at reduced pressure, and the resulting residue was poured into iced saturated $NH_4Cl$. The mixture was extracted with ether and the ether solution washed with additional saturated $NH_4Cl$. The ether solution was dried over magnesium sulfate and evaporated to dryness at reduced pressure to afford 338 g of crude 2-benzyl-1,3,4-trimethyl-1,2-dihydropyridine.

The Grignard diene intermediate was then efficiently reduced to the corresponding 2-benzyl-1,3,4-trimethyl-1,2,5,6-tetrahydropyridine analog. To a solution of the crude dihydropyridine product in 2.0 L of 100% ethanol was added portionwise 37.8 g of $NaBH_4$. The reaction mixture was refluxed for 2 hrs and then cooled to room temperature. The reaction mixture was quenched by the slow addition of concentrated HCl until a pH of 2 was maintained. The ethanol was evaporated at reduced pressure, the resultant residue was dissolved in ether and water. The aqueous phase was separated and brought to pH 11 by the portionwise addition of solid NaOH pellets. The aqueous phase was extracted with ether. The ether solution was dried over $MgSO_4$ and evaporated to dryness at reduced pressure to afford 200 g of crude 2-benzyl-1,3,4-trimethyl-1,2,5,6-tetrahydropyridine (59% yield).

The cyclization of the tetrahydropyridine proceeded smoothly in 48% HBr. A solution of 195 g of 2-benzyl-1,3,4-trimethyl-1,2,5,6-tetrahydropyridine in 2500 mL of 48% HBr was heated to slightly below reflux for 48 hrs. The reaction mixture was poured into $H_2O$ and extracted with ether. To the aqueous solution was added slowly NaOH pellets to pH 11. The aqueous solution was then extracted with ether. The ether solution was dried over MgSO$_4$ and evaporated to dryness at reduced pressure to afford 185 g of crude material. The crude product was purified by vacuum distillation to obtain 69.8 g of 2,5,9-trimethyl-6,7-benzomorphan (($\pm$)-IIId-5) (36% yield).

$^1$H NMR (CDCl$_3$, 300 MHz) $\delta$7.0–7.30 (m, 4H aromatic), 2.4 (s, 3H, N—CH$_3$), 1.38 (s, 3H, C$_5$—CH$_3$), 0.85 (d, J=7 Hz, C$_9$—CH$_3$).

Resolution of 2,5,9-Trimethyl-6,7-benzomorphan (($\pm$)-IIId-5) and preparation of HCl salt of (1S,5S,9S)-(+)-2,5,9-trimethyl-6,7-benzomorphan ((+)-IIId-5 HCl)

To a solution of racemic ($\pm$)-IIId-5 (67.1 g, 0.312 mol) in 200 mL ethanol at room temperature was added a solution of (−)-L-ditoluoyl-tartaric acid (120.74 g, 0.312 mol) in 1000 mL of ethanol. On standing, a crop of salt crystals formed which was collected and vacuum-dried. Yield: 98.41 g, 104% theory. This material was dissolved in 600 mL of ethanol at reflux. Then the solution was let cool to room temperature and pure (+)-IIId-5 was recovered as the ditoluoyl tartrate salt: 52.74 g, 0.087 mol, 52% theory. This material was partitioned in ether/0.1N aqueous NaOH and the ether-layer was separated, dried over MgSO$_4$, filtered and treated with a solution of HCl in anhydrous ether to produce a mass of ($\pm$)-IIId-5.HCl as the white powder (20.5 g, 86.4 mmol, 98% from ditoluoyl tartrate salt). Rotation of (+)-IIId-5.HCl: $[\alpha]_D^{25} = +43.4°$ ($\pm 0.4°$) (c=1, EtOH)

Example 2

Synthesis of (1S,5S,9S)-(+)-5,9-Dimethyl-6,7-benzomorphan ((+)-IIId-4) and HCl salt thereof ((+)-IIId-4.HCl)

As shown in Scheme 3 (FIG. 3), to a solution of (+)-IIId-5 (2.18 g, 9.42 mmol, Example 1) in 80 mL of dry 1,2-dichloroethane was added freshly distilled $\alpha$-chloroethyl chloroformate (ACE-Cl, 5.86 g, 40.9 mmol) and the mixture stirred at reflux for 3 hrs. Then, K$_2$CO$_3$ powder (6.0 g, 43 mmol) was added and reflux continued for another 18 hrs. Then the slurry was filtered, spin-evaporated, and the residue dissolved in 30 mL of methanol. This solution was heated to reflux for 10 min, then spin-evaporated to give crude (+)-IIId-4.HCl as a gum. The gum was dissolved in ethyl acetate/ether (1:1, 40 mL) and pure (+)-IIId-4.HCl crystallized: wt. 1.91 g, 79% yield.

Rotation of (+)-IIId-4.HCl: $[\alpha]_D^{25} = +32.5°$ ($\pm 0.2°$) (c=1, EtOH).

$^1$H NMR (CD$_3$OD, 300 MHz) $\delta$7.37–7.15 (m, 4H, aromatic), 3.75 (brs, 1H, C$_1$—H), 1.47 (s, 3H, C$_5$—CH$_3$), 0.92 (d, 3H, C$_9$—CH$_3$).

Example 3

Synthesis of (1S,5S,9S)-(+)-2-Isopropyl-5,9-dimethyl-6,7-benzomorphan ((+)-IIId-6) and HCl salt thereof ((+)-IIId-6.HCl)

As shown in Scheme 3 (FIG. 3), a mixture of (+)-IIId-4.HCl (1.00 g, 3.94 mmol, Example 2) in acetone (50 mL) at reflux was treated with sodium cyanoborohydride (NaCNBH$_3$, 0.55 g, 8.7 mmol). After 3 hrs, reaction was completed. Following a workup, the crude product (+)-IIId-6 was purified by flash chromatography (silica gel/ethyl acetate) and recovered. The product was crystallized from ether/dichloromethane as a white powder (wt. 1.02 g, 4.2 mmol, crude yield 99%). This free base was converted to the HCl salt in ether with HCl/ether treatment to produce a white powder (+)-IIId-6.HCl, 0.946 g, 3.4 mmol, yield 80%.

Rotation of (+)-IIId-6.HCl: $[\alpha]_D^{25} = +53.1°$ ($\pm 0.2°$) (c=1, EtOH)

$^1$H NMR (CD$_3$OD, 300 MHz) $\delta$7.37–7.15 (m, 4H, aromatic), 3.89 (brs, 1H, C$_1$—H), 1.48 (s, 3H, C$_5$—CH$_3$), 1.41 (d, 6H, CH$_3$ of i-propyl), 0.96 (d, 3H, C$_9$—CH$_3$).

Example 4

Synthesis of (1S,5S,9S)-(+)-2-(1-cyclopropylethyl)-5,9-dimethyl-6,7-benzomorphan ((+)-IIId-7) and HCl salt thereof ((+)-IIId-7.HCl)

As shown in Scheme 4 (FIG. 4), (+)-IIId-7 and (+)-IIId-7.HCl can be prepared in the following two ways, Method A and Method B. Method B gives a higher yield.

Method A: Reductive alkylation

To a solution of (+)-IIId-4.HCl (0.53 g, 2.09 mmol, Example 2) in 40 mL methylcyclopropyl ketone at 93° C. under argon was added with stirring NaCNBH$_3$ (2.00 g, 31.7 mmol). Then glacial acetic acid was added dropwise until H$_2$ evolution ceased over an approximately 2 hr period. Following a routine workup, the crude product was purified by flash chromatography (silica gel/ethyl acetate). The isolated free base (+)-IIId-7 was dissolved in ether and precipitated as the HCl salt by addition of HCl/ether solution: (+)-IIId-7.HCl, wt. 0.32 g, 47% yield.

Method B: Grignard alkylation

A mixture of (+)-IIId-4 (1.27 g, 5.84 mmol, Example 2) and lactonitrile (0.58 g, 8.2 mmol) in 30 mL of dichloromethane was stirred at room temperature for 3 hrs, then washed with H$_2$O, and aqueous-layer separated, dried over MgSO$_4$, and evaporated to afford the cyanoamine intermediate 5 (1.59 g, 6.3 mmol, 99%). The cyanoamine 5 (1.59 g, 6.3 mmol) was dissolved in 50 mL dry THF and treated with a solution of cyclopropyl magnesium bromide in excess in THF at room temperature. After workup and purification on silica gel, (+)-IIId-7 was recovered as a mixture of diastereomers, 1.40 g, 5.2 mmol, yield 83%. When treated with HCl/ether, the product (+)-IIId-7.HCl precipitated as a white powder from ether, 1.41 g, yield 77%.

Separations of the diastereomers of (+)-IIId-7 (1.15 g) were carried out on 150 mL of flash silica gel and elution with hexanes/ethyl acetate/triethylamine (7:1:1%) to give isomer A and isomer B of (+)-IIId-7.

Acidification with hydrochloric acid in ether and filtration afforded the corresponding hydrochloride salts, isomer A of (+)-IIId-7.HCl (0.48 g) and isomer B of (+)-IIId-7.HCl (0.56 g).

Isomer A of (+)-IIId-7 $^1$H NMR: (CDCl$_3$, 300 MHz) $\delta$7.22–6.95 (m, 4H, aromatic), 1.34 (s, 3H, C$_5$—CH$_3$), 1.13 (d, 3H, $\alpha$-CH$_3$), 0.81 (d, 3H, C$_9$—CH$_3$), 0.71–0.00 (m, 5H, cyclopropyl). MS: m/z=269 (parent ion), 254 (M-CH$_3$) 228 (M-cyclopropyl).

| Elem. Anal. (Isomer A of (+)IIId-7.HCl.$\frac{1}{4}$H$_2$O): | | | |
| --- | --- | --- | --- |
| | % C | % H | % N |
| Calc. | 73.52 | 9.25 | 4.51 |
| Found | 73.21 | 8.99 | 4.40 |

Isomer B of (+)IIId-7 ¹H NMR: (CDCl₃, 300 MHz) δ7.27–7.00 (m, 4H, aromatic), 1.36 (s, 3H, C₅—CH₃), 1.25 (d, 3H, α-CH₃), 0.85 (d, 3H, C₉—CH₃), 0.75–0.00 (m, 5H, cyclopropyl). MS: m/z=269 (parent ion), 254 (M-CH₃), 228 (M-cyclopropyl).

Example 5

Synthesis of (1S,5S,9S)-(+)-2-Dicyclopropylmethyl-5,9-dimethyl-6,7-benzomorphan ((+)-BZ-1) and HCl salt thereof ((+)-BZ-1.HCl)

As shown in Scheme 5 (FIG. 5), 2.54 g (12.60 mmol) of (+)-IIId-4 (Example 2) was treated with 1.46 g (15.12 mmol) of cyclopropanecarbaldehyde cyanohydrin 6 in 100 mL of dichloromethane for 3 hrs at room temperature. The cyclopropanecarbaldehyde cyanohydrin 6 was prepared in 61% yield from cyclopropyl methanol by Swern oxidation and treatment of the crude cyclopropanecarbaldehyde with 1 equivalent of acetone cyanohydrin in dichloromethane for 2 hrs at room temperature. Workup, as above, afforded 3.52 g (99%) of the aminonitrile 7. Treatment of 1.76 g (6.25 mmol) of 7 in 50 mL of THF with cyclopropyl magnesium bromide (prepared from 2.00 g (16.5 mmol) of cyclopropyl bromide and 1.3 g (53.5 mmol) of magnesium powder) afforded, after stirring for 2 hrs at room temperature and workup, the crude product mixtures. Purification by flash column chromatography on 100 mL of silica gel and elution with hexanes/ethylacetate/triethylamine (5:1:1) afforded 1.69 g (91%) of (+)-BZ-1 as oils. Acidification with hydrochloric acid in ether and filtration afforded the corresponding hydrochloride salts (+)-BZ-1.HCl as colorless crystalline solids.

(+)-BZ-1 ¹H NMR: (CDCl₃, 300 MHz) δ6.95–6.70 (m, 4H, aromatic), 3.40 (brs, 1H, C₁—H), 1.08 (s, 3H, C₅—CH₃), 0.52 (d, 3H, C₉—CH₃), 0.30–0.00 (m, 10H, cyclopropyl). MS: m/z=295 (parent ion), 280 (M-CH₃), 254 (M-cyclopropyl).

| Elem. Anal. ((+)-BZ-1.HCl.H₂O): | | | |
|---|---|---|---|
| | % C | % H | % N |
| Calc. | 73.98 | 9.7 | 4.11 |
| Found | 74.32 | 9.26 | 3.96 |

Example 6

Synthesis of (1S,5S,9S)-(+)-5,9-Dimethyl-2-(1-methyl-2-propenyl)-6,7-benzomorphan ((+)-BZ-2) and HCl salt thereof (+)-BZ-2.HCl)

As shown in Scheme 6 (FIG. 6), the aminonitrile 5 (1.59 g, 6.25 mmol, Example 4) was dissolved in 50 mL of dry THF and treated with 12.5 mL (12.5 mmol, 1M solution in THF) of vinyl magnesium bromide (Aldrich). The reaction mixture was stirred for 2 hrs at room temperature, extracted with dichloromethane, washed with water, dried (K₂CO₃), filtered, and concentrated to give crude product mixture. Purification by flash column chromatography on 100 mL of silica gel and elution with hexanes/ethylacetate/triethylamine, 5:1:1, afforded 1.40 g (87%) of (+)-BZ-2 as oils. Acidification with hydrochloric acid in ether and filtration afforded the corresponding hydrochloride salts (+)-BZ-2.HCl as colorless crystalline solids.

(+)-BZ-2 ¹H NMR: (CDCl₃, 300 MHz) δ7.27–7.03 (m, 4H, aromatic), 5.87–5.67 (m, 1H, vinyl), 5.21–4.95 (m, 2H, vinyl), 1.40 (s, 3H, C₅—CH₃), 1.20, 1.16 (2d, 3H, α-CH₃ isomers), 0.85, 0.81 (2d, 3H, C₉—CH₃ isomers). MS: m/z=255 (parent ion), 240 (M-CH₃), 228 (M-vinyl).

| Elem. Anal. ((+)-BZ-2.HCl): | | | |
|---|---|---|---|
| | % C | % H | % N |
| Calc. | 74.08 | 8.98 | 4.80 |
| Found | 74.31 | 8.71 | 4.59 |

Example 7

Synthesis of (1S,5S,9S)-(+)-2-(1-Cyclobutylethyl)-5,9-dimethyl-6,7-benzomorphan ((+)-BZ-3) and HCl salt thereof ((+)-BZ-3.HCl)

As shown in Scheme 7 (FIG. 7), the aminonitrile 5 (1.59 g, 6.25 mmol, Example 4) was dissolved in 50 mL of dry THF and treated with cyclobutyl magnesium bromide (prepared from 3.0 g (22.2 mmol) of cyclobutyl bromide and 1.5 g (61.7 mmol) of magnesium powder). The reaction mixture was stirred for 2 hrs at room temperature, extracted with dichloromethane, washed with water, dried (K₂CO₃), filtered, and concentrated to give crude product mixture. Purification by flash column chromatography on 100 mL of silica gel and elution with hexanes/ethylacetate/triethylamine, 5:1:1, afforded 1.50 g (84%) of (+)-BZ-3 as oils. Acidification with hydrochloric acid in ether and filtration afforded the corresponding hydrochloride salts (+)-BZ-3.HCl as colorless crystalline solids. Separation of 0.90 g of the mixture of the diastereomers of (+)-BZ-3 was carried out on 150 mL of flash silica gel and elution with hexanes/ethyl acetate/triethylamine (7:1:1%) to give isomer A and 0.29 g of isomer B of (+)-BZ-3.

Acidification with hydrochloric acid in ether and filtration afforded the corresponding hydrochloride salts, isomer A of (+)-BZ-3.HCl (0.25 g) and isomer B of (+)-BZ-3.HCl (0.30 g).

Isomer A of (+)-BZ-3 ¹H NMR: (CDCl₃, 300 MHz) δ7.25–7.03 (m, 4H, aromatic), 3.07 (brs, 1H, C₁—H), 1.36 (s, 3H, C₅—CH₃), 0.95 (d, 3H, α-CH₃), 0.81 (d, 3H, C₉—CH₃). MS: m/z=283 (parent ion), 268 (M-CH₃), 228 (M-cyclobutyl).

| Elem. Anal. (Isomer A of (+)-BZ-3.HCl.½H₂O): | | | |
|---|---|---|---|
| | % C | % H | % N |
| Calc. | 74.05 | 9.48 | 4.32 |
| Found | 74.06 | 9.29 | 4.32 |

Isomer B of (+)-BZ-3 ¹H NMR: (CDCl₃, 300 MHz) δ7.27–7.03 (m, 4H, aromatic), 3.10 (brs, 1H, C₁—H), 1.36 (s, 3H, C₅—CH₃), 0.96 (d, 3H, α-CH₃), 0.82 (d, 3H, C₉—CH₃).

Example 8

Synthesis of (1S,5S,9S)-(+)-2-(1Cyclopropyl-2-propenyl)-5,9-dimethyl-6,7-benzomorphan ((+)-BZ-4) and HCl salt thereof ((+)-BZ-4.HCl)

As shown in Scheme 8 (FIG. 8), treatment of 1.76 g (6.25 mmol) of 7 (Example 5) in 50 mL of THF with 12.5 mL (12.5 mmol, 1M solution in THF) of vinyl magnesium bromide afforded, after stirring for 2 hrs at room temperature and workup, the crude product mixture. Purification by flash column chromatography on 100 mL of silica gel and elution with hexanes/ethylacetate/triethylamine (5:1:1) afforded 1.57 g (88%) of (+)-BZ-4 as oils. Acidification with hydrochloric acid in ether and filtration afforded the corresponding hydrochloride salts (+)-BZ-4.HCl as colorless crystalline solids.

(+)-BZ-4 $^1$H NMR: (CDCl$_3$, 300 MHz) $\delta$7.25–7.00 (m, 4H, aromatic), 5.90–5.70 (m, 1H, vinyl), 5.10–4.88 (m, 2H, vinyl), 1.38 (s, 3H, C$_5$—CH$_3$), 0.86, 0.81 (2d, 3H, C$_9$—CH$_3$ (isomers)), 0.80–0.00 (m, 5H, cyclopropyl) MS: m/z=281 (parent ion), 266 (M-CH$_3$), 254 (M-vinyl), 240 (M-cyclopropyl).

| Elem. Anal. ((+)-BZ-4.HCl.½H$_2$O): | | | |
|---|---|---|---|
| | % C | % H | % N |
| Calc. | 74.51 | 8.91 | 4.34 |
| Found | 74.82 | 8.86 | 4.26 |

Example 9

Synthesis of (1S,5S,9S)-(+)-5,9-Dimethyl-2-(1-methyl-2-propynyl)-6,7-benzomorphan ((+)-BZ-6) and HCl salt thereof ((+)-BZ-6.HCl)

As shown in Scheme 9 (FIG. 9), the aminonitrile 5 (1.59 g, 6.25 mmol, Example 4) was dissolved in 50 mL of dry THF and treated with 25.0 mL (12.5 mmol, 0.5M solution in THF) of ethyl magnesium chloride (Aldrich). The reaction mixture was stirred for 2 hrs at room temperature, extracted with dichloromethane, washed with water, dried (K$_2$CO$_3$), filtered, and concentrated to give crude product mixture. Purification by flash column chromatography on 100 mL of silica gel and elution with hexanes/ethylacetate/triethylamine, 5:1:1, afforded 0.65 g (41%) of isomer A of (+)-BZ-6, and 0.65 g (41%) of isomer B of (+)-BZ-6 as oils. Acidification with hydrochloric acid in ether and filtration afforded the corresponding hydrochloride salts, isomer A of (+)-BZ-6.HCl and isomer B of (+)-BZ-6.HCl as colorless crystalline solids.

Isomer A of (+)-BZ-6 $^1$H NMR (CDCl$_3$, 300 MHz) $\delta$7.27–7.00 (m, 4H, aromatic), 1.38 (dd, 3H, $\alpha$-CH$_3$), 1.36 (s, 3H, C$_5$—CH$_3$), 0.82 (d, 3H, C$_9$—CH$_3$). MS: m/z=253 (parent ion), 238 (M-CH$_3$).

| Elem. Anal. (Isomer A of BZ-6.HCl): | | | |
|---|---|---|---|
| | % C | % H | % N |
| Calc. | 74.59 | 8.35 | 4.83 |
| Found | 74.82 | 8.33 | 4.87 |

Isomer B of (+)-BZ-6 $^1$H NMR (CDCl$_3$, 300 MHz) $\delta$7.25–7.00 (m, 4H, aromatic), 1.43 (dd, 3H, $\alpha$-CH$_3$), 1.36 (s, 3H, C$_5$—CH$_3$), 0.86 (d, 3H, C$_9$—CH$_3$). MS: m/z=253 (parent ion), 238 (M-CH$_3$).

| Elem. Anal. (Isomer B of (+)-BZ-6.HCl): | | | |
|---|---|---|---|
| | % C | % H | % N |
| Calc. | 74.59 | 8.35 | 4.83 |
| Found | 74.51 | 8.56 | 4.75 |

Example 10

Synthesis of (1S,5S,9S)-(+)-5,9-Dimethyl-2-(1-methyl-2,3-epoxypropyl)-6,7-benzomorphan ((+)-BZ-5) and HCl salt thereof ((+)-BZ-5.HCl)

As shown in Scheme 10 (FIG. 10), the synthesis of the epoxyamine (+)BZ-5, which has two new chiral centers, was carried out using two schemes leading to a mixture of aminodiols, followed by cyclodehydration to afford isomer A of (+)-BZ-5 and a mixture of isomers B and C of (+)-BZ-5. The approach to isomer A of (+)-BZ-5 utilized a method developed by Sharpless et al. (J. Org. Chem., 51: 1922, (1986)). In this scheme, trans-2-buten-1-ol was stereoselectively epoxidized with t-butyl hydroperoxide in dichloromethane in the presence of catalytic L-(+)-diethyltartrate and titanium (IV) isopropoxide. To a mixture of 0.40 g (4.5 mmol) of the 2S,3S-oxirane and 0.60 g (3.0 mmol) of (+)IIId-4 (Example 2) in 8 mL of dichloromethane was added 2.0 mL (6.8 mmol) of titanium (IV) isopropoxide, and stirring was continued for 16 h at room temperature. The solvent was evaporated to an oil, then 15 mL of ether was added followed by 3 mL of 10% NaOH in brine. The mixture was vigorously stirred for 15 h at room temperature, filtered through celite, dried (K$_2$CO$_3$), filtered, concentrated and purified on silica gel to give 0.81 g (93%) of the pure aminodiol 8 (Sharpless et al., J. Org. Chem., 50: 1557 (1985)). A mixture of 0.26 g (0.90 mmol) of the aminodiol 8 and 0.31 mL (2.2 mmol) of triethylamine in 35 mL of THF was treated with 0.11 g (0.95 mmol) of methanesulfonyl chloride in 3 mL of dichloromethane at −78° C. for 0.5 h and at 0° C. for 1 h. Then 2.3 mL (2.3 mmol) of a 1N solution of sodium methoxide in methanol was added. The mixture was stirred at 0° C. for 2 h and at room temperature for 1 h. The solvent was evaporated, and the residue was extracted with dichloromethane, dried, filtered, and concentrated to give 0.14 g of an oil. Purification by flash column chromatography on 30 mL of silica gel and elution with hexanes/ethyl acetate/triethylamine (3:1:1%) afforded 96 mg (40%) of isomer A of (+)-BZ-5 as a single diastereomer. Acidification with hydrochloric acid in ether and filtration afforded 99 mg of the hydrochloride salt as a colorless solid.

A second approach to the epoxyamine (+)BZ-5 involves reaction of 0.60 g (3.0 mmol) of (+)IIId-4 (Example 2) with 0.55 g (3.5 mmol) of the cyanohydrin, which was prepared by protection of glycerol as the acetonide (Org. Syn., Coll. vol. 2, p. 502), followed by Swern oxidation of the free alcohol and treatment of the aldehyde with acetone cyanohydrin and catalytic triethylamine. The mixture was stirred for 1 day at room temperature in 20 mL of dichloromethane and worked up to give 1.16 g of the aminonitrile 9, which was reacted with 2.0 mL (6.0 mmol) of 3N methyl magnesium bromide in 25 mL of THF with stirring for 15 h at room temperature. Workup and treatment of the crude product mixture with 1.0 mL of 12N HCl in 11mL of methanol with stirring for 2 h at room temperature followed by treatment with 3 mL of 6N NaOH and workup gave 0.72 g of the crude product mixture. Purification by flash column chromatography on 50 mL of silica gel and elution with ethyl acetate/methanol/triethylamine (9:1:1%) afforded a total of 0.56 g (64%) of the aminodiol 10. Four diastereomers were visible by tlc, and were collected in two fractions containing two unseparated diastereomers in each fraction, weighing 0.28 g in both cases. Treatment of 0.28 g (0.97 mmol) of the less polar fraction with mesyl chloride/triethylamine followed by sodium methoxide/methanol and purification as above afforded 99 mg (38%) of a mixture of isomers B and C of (+)-BZ-5 and 110 mg of the HCl salt.

Isomer A of (+)-BZ-5 $^1$H NMR: (CDCl$_3$, 300 MHz) $\delta$7.0–7.3 (m, 4H, aromatic), 3.20 (brs, 1H, C$_1$—H), 1.40 (s, 3H, C$_5$—CH$_3$) 1.25 (d, 3H, $\alpha$-CH$_3$), 0.85 (d, 3H, C$_9$—CH$_3$). MS: m/z=271 (parent ion), 256 (M-CH$_3$), 228 (M-oxirane (C$_2$H$_3$O)).

| Elem. Anal. (Isomer A of (+)-BZ-5.HCl): | | | |
|---|---|---|---|
| | % C | % H | % N |
| Calc. | 69.80 | 8.47 | 4.28 |
| Found | 70.23 | 8.51 | 4.55 |

Isomers B and C of (+)-BZ-5 (mixture of diastereomers ~2:1) $^1$H NMR: (CDCl$_3$, 300 MHz) $\delta$7.0–7.3 (m, 4H, aromatic), 3.46 & 3.16 (brs, 1H, C$_1$—H (isomers ~1:2)), 1.40 (s, 3H, C$_5$—CH$_3$), 1.15–1.25 (2d, 3H, $\alpha$-CH$_3$ (2-isomers)), 0.8–0.9 (2d, 3H, C$_9$—CH$_3$ (2 isomers)).

Example 11

Synthesis of
(1S,5S,9S)-(+)-2'-Fluoro-2-isopropyl-5,9-dimethyl-6,7-benzomorphan (+)-BZ-13) and HCl salt thereof
((+)-BZ-13.HCl)

(+)-BZ-10.HCl was prepared in the manner of the synthesis of (+)-IIId-4.HCl (FIG. 2 and 3) using p-fluorobenzylmagnesium bromide instead of benzylmagnesium chloride.

As shown in Scheme 11 (FIG. 11), reductive alkylation of 0.35 g (1.4 mmol) of (+)BZ-10.HCl with 0.30 g (4.8 mmol) of sodium cyanoborohydride in 50 mL of acetone for 2 h at reflux afforded, after workup and purification by flash column chromatography of the crude product mixture on 50 mL of silica gel and elution with hexanes/ethyl acetate/triethylamine (1:1:1%), 0.36 g (99%) of (+)-BZ-13. Acidification with hydrochloric acid in ether and filtration afforded the HCl salt as a colorless crystalline solid.

(+)-BZ-13. HCl: $^1$H NMR: (CDCl$_3$, 300 MHz) $\delta$1.14, 1.12 (2d, 6H, CH$_3$ of i-Pr) MS: m/z=261 (parent ion), 246 (M-CH$_3$),

| Elem. Anal. (CHN) for C$_{17}$H$_{25}$NClF | | | |
|---|---|---|---|
| | % C | % H | % N |
| Calc. | 68.56 | 8.46 | 4.70 |
| Found | 68.47 | 8.65 | 4.78 |

Example 12

Synthesis of
(1S,5S,9S)-(+)-2-(1-Cyclopropylethyl)-2'-fluoro-5,9-dimethyl-6,7-benzomorphan (+)-BZ-14) and HCl salt thereof (+)-BZ-14.HCl)

As shown in Scheme 12 (FIG. 12), reaction of 0.66 g (3.0 mmol) of (+)-BZ-10 (Example 11) with 0.36 g (3.6 mmol) of cyclopropylmethyl carboxaldehyde cyanohydrin in 20 mL of dichloromethane for 3 h at room temperature followed by extractive workup gave 0.92 g (99%) of the aminonitrile. Treatment of the aminonitrile with 2.0 mL (6.0 mmol) of methyl magnesium bromide in 20 mL of THF for 3 h at room temperature followed by extractive workup gave 1.01 g of the crude (+)BZ-14 mixture. Purification by flash column chromatography on 150 mL of silica gel and elution with hexanes/ethyl acetate/triethylamine (7:1:1%) afforded 0.25 g (29%) of isomer A of (+)-BZ-14, and 0.38 g of isomer B of (+)-BZ-14 as oils. Acidification with hydrochloric acid in ether and filtration provided the corresponding HCl salts as colorless crystalline solids, respectively.

Isomer A of (+)-BZ-14 $^1$H NMR (CDCl$_3$, 300 MHz) $\delta$6.7–7.0 (m, 3H, aromatic) 3.65 (brs, 1H, C$_1$—H), 2.84 (d, 1H, C$_8$—H), 2.7 (m, 1H, C$_\alpha$—H), 1.33 (s, 3H, C$_5$—CH$_3$), 1.17 (d, 3H, $\alpha$-CH$_3$), 0.80 (d, 3H, C$_9$—CH$_3$), −0.2–0.7 (m, 5H, cyclopropyl). MS: m/z=287 (parent ion), 272 (M-CH$_3$), 246 (M-cyclopropyl )

| Elem. Anal. of Isomer A of (+)-BZ-14.HCl: | | | |
|---|---|---|---|
| | % C | % H | % N |
| Calc. | 70.46 | 8.40 | 4.32 |
| Found | 70.19 | 8.51 | 4.31 |

Isomer B of (+)-BZ-14 $^1$H NMR (CDCl$_3$, 300 MHz) $\delta$6.75–7.05 (m, 3H, aromatic), 3.30 (m, 1H, C$_\alpha$—H), 3.23 (brs, 1H, C$_1$—H), 2.86 (d, 1H, C$_8$ —H), 2.65 (dd, 1H, C$_8$—H), 1.36 (s, 3H, C$_5$—CH$_3$), 1.25 (d, 3H, $\alpha$-CH$_3$), 0.85 (d, 3H, C$_9$—CH$_3$), −0.2–0.75 (m, 5H, cyclopropyl) MS: m/z=257 (parent ion), 242 (M-CH$_3$)

Example 13

Synthesis of
(1S,5S,9S)-(+)-2-Tert-butyl-5,9-dimethyl-6,7-benzomorphan ((+)-BZ-15A) and HCl salt thereof
((+)-BZ-15A.HCl)

As shown in Scheme 13 (FIG. 13), a mixture of 0.25 g (1.3 mmol) of (+)IIId-4 (Example 2) and 2.0 g (23.5 mmol) of acetone cyanohydrin was heated at 72° C. for 0.5 h, then 0.9 g of additional acetone cyanohydrin was added and stirring at 72° C. was continued for an additional 0.3 h. After cooling, the mixture was extracted with dichloromethane versus water, dried (K$_2$CO$_3$), filtered, and concentrated to give 0.39 g (90%) of the aminonitrile. Treatment of the aminonitrile with 2.0 mL (6.0 mmol) of 3N methyl magnesium bromide in 10 mL of THF for 15 h at room temperature followed by extractive workup gave 0.32 g of the crude product mixture. Purification by flash column chromatography on 30 ml of silica gel and elution with hexanes/ethyl acetate/triethylamine (3:1:1%) afforded 0.23 g (70%) of (+)BZ-15A. Acidification with hydrochloric acid in ether and filtration provided the HCl salt as a colorless solid.

(+)-BZ-15A $^1$H NMR (CDCl$_3$, 300 MHz) $\delta$7.05–7.3 (m, 4H, aromatic) 3.32 (brs, 1H, C$_1$—H), 1.40 (s, 3H, C$_5$—CH$_3$), 1.18 (s, 9H, t-butyl), 0.83 (d, 3H, C$_9$—CH$_3$) MS: m/z=257 (parent ion), 242 (M-CH$_3$)

| Elem. Anal. (+)-BZ-15A.HCl | | | |
|---|---|---|---|
| | % C | % H | % N |
| Calc. | 73.57 | 9.60 | 4.77 |
| Found | 73.43 | 9.65 | 4.57 |

Example 14

Synthesis of (1S,5S,9S)-(+)-2-hydroxy-5,9-dimethyl-6,7-benzomorphan ((+)-BZ-17A) and HCl salt thereof ((+)-BZ-17A.HCl)

As shown in Scheme 14 (FIG. 14), an approach suggested by Rogers, (J. Chem. Soc., p. 769, (1955)), (+)IIId-4.HCl (Example 2) (0.521 g, 2.19 mmol) in CHCl$_3$ (40 mL) was treated with ethyl acrylate (0.438 g, 20 eq) and triethylamine (0.66 g, 3.0 eq) at reflux for 16 h. TLC then showed nearly complete conversion to a new, nonpolar product. After filtration through a silica pad and spin evaporation, the adduct 11 was recovered as a colorless oil (0.49 g, 74%). Treatment of 11 (0.49 g, 1.63 mmol) in CHCl$_3$ (10 mL) at room temperature with 50% m-chloroperbenzoic acid (0.52 g, 1.5 eq peroxide) with stirring for 1 h followed by brief spin-evaporation of the reaction mixture up to $-100°$ C. (a heat gun was used to drive off volatiles, ethyl acrylate), a crude product was isolated (0.72 g) as a yellow gum. TLC showed no starting material and a major higher $R_f$ spot. This product was partitioned in 1N K$_2$CO$_3$—H$_2$O/ether to remove benzoic acids, and the organic layer was separated, dried, and evaporated to afford crude (+)BZ-17A (0.296 g, 89%). Treatment of (+)BZ-17A (0.20 g, 1.36 mmol) in ether with HCl/ether produced (+)BZ-17A.HCl as a white powder (0.274 g, 79%).

(+)-BZ-17A $^1$H NMR (CDCl$_3$, 300 MHz) δ7.4—7.1 (m, 4H, aromatic), 3.38 (brs, 1H, C$_1$—H), 1.95 (s, 3H, C$_5$—CH$_3$), 0.86 (d, 3H, C$_9$—CH$_3$). (+) -BZ-17A.HCl MS: m/z=217 (parent ion), 200 (M-OH).

| Elem. Anal. (+)-BZ-17A.HCl: | | | | |
|---|---|---|---|---|
| | % C | % H | % N | % Cl |
| Calc. | 66.26 | 7.94 | 5.52 | 13.97 |
| Found | 66.37 | 8.03 | 5.36 | 13.77 |

Example 15

Synthesis of (1S,5S,9S)-(+)-5,9-dimethyl-2-dimethylamino-6,7-benzomorphan ((+)-BZ-18) and HCl Salt thereof ((+)-BZ-18.HCl)

As shown in Scheme 15 (FIG. 15), (+)IIId-4.HCl (Example 2) (0.60 g, 2.52 mmol) was dissolved in 70 m/L of methanol and treated with a solution of K$_2$CO$_3$ (2.1 g, 15.2 mmol) in 20 mL of H$_2$O and heated to reflux. Then hydroxylamine-O-sulfonic acid (H$_3$N$^+$-OSO$_3^-$, 0.42 g, 3.07 mmol, 1.5 eq) was added in 3 equal portions (0.14 g) over 20 min. The reaction mixture was filtered to remove insoluble inorganic salts (K$_2$SO$_4$), the filtrate was spin-evaporated to remove methanol, and the aqueous residue was partitioned in CH$_2$Cl$_2$/H$_2$O. The organic layer containing 12, unreacted (+)IIId-4, and other by-products was spin-evaporated to give a yellow oily residue (0.48 g). This material was immediately dissolved in 10 mL of H$_2$O, acidified to pH 3, and treated with 1.0 mL of 37% aqueous formalin, followed by NaCNBH$_3$ (0.49 g, 7.6 mmol). TLC after 5 min showed that no 12 or (+)IIId-4 remained. Then 3N HCl was added to quench excess NaCNBH$_3$, and the reaction mixture was washed with ether to remove impurities at high $R_f$. The aqueous layer was basified and crude (+)BZ-18 was isolated along with (+)IIId-5 (Example 1) (resulting from N-methylation of IIId-4). Filtration through silica readily separated the less polar (+)BZ-18 from (+)IIId-5 (eluting with CH$_2$Cl$_2$, then ether) to afford pure (+)BZ-18 (0.28 g, 1.14 mmol, 45% from (+)IIId-4.HCl). The NMR was quite clean, the N—N(CH$_3$)$_2$ peak at δ2.488 was very distinctive, and no other N—Me peak was observed. MS showed the expected parent ion at m/z 244 and major fragments at m/z 229 (—Me), and 200 (—N(CH$_3$)$_2$). The HCl salt was then produced as a white powder by treatment with HCl/ether: (+)-BZ-18.HCl (0.2 g, 0.72 mmol, 31% from (+)IIId-4.HCl).

(+)-BZ-18 $^1$H NMR (CHCl$_3$, 300 MHz) δ7.05–7.25 (m, 4H, aromatic), 3.22 (dd, 1H, C$_1$—H), 2.49 (s, 6H, N(CH$_3$)$_2$), 1.36 (s, 3H, C$_5$—CH$_3$), 0.84 (d, 3H, C$_9$—CH$_3$). MS: m/z=244 (parent ion), 229 (M-CH$_3$), 200 (M-N(CH$_3$)$_2$).

| Elem. Anal. ((+)-BZ-18.HCl): | | | |
|---|---|---|---|
| | % C | % H | % N |
| Calc. | 68.36 | 9.26 | 9.97 |
| Found | 68.11 | 8.96 | 9.68 |

Example 16

Synthesis of (1S,5S,9S)-(+)-2'-Chloro-2-isopropyl-5,9-dimethyl-6,7-benzomorphan ((+)-BZ-26) and HCl salt thereof ((+)-BZ-26.HCl)

(+)-BZ-23.HCl was prepared in the manner of the synthesis of (+)-IIId-4.HCl (FIG. 2 and 3) using p-chlorobenzylmagnesium bromide instead of benzylmagnesium chloride.

As shown in Scheme 16 (FIG. 16), reductive alkylation of 0.27 g (1.0 mmol) of (+)BZ-23.HCl with 0.25 g (4.0 mmol) of sodium cyanoborohydride in 40 mL of acetone for 2 h at reflux afforded, after workup and purification of the crude product mixture by flash column chromatography on 30 mL of silica gel and elution with hexanes/ethyl acetate/triethylamine (1:1:1%), 0.25 g (90%) of (+)BZ-26. Acidification with hydrochloric acid in ether and filtration provided the HCl salt.

(+) -BZ-26.HCl $^1$H NMR (CDCl$_3$, 300 MHz) δ7.20 (d, 1H, aromatic), δ7.0 (m, 2H, aromatic), 3.20 (brs, 1H, C$_1$—H), 1.35 (s, 3H, C$_5$—CH$_3$), 1.12 (2d, 6H, CH$_3$ of i-Pr) 0.82 (d, 3H, C$_9$—CH$_3$). MS: m/z=279, 277 (parent ion), 264, 262 (M-CH$_3$)

| Elem. Anal. BZ-26.HCl: | | | |
|---|---|---|---|
| | % C | % H | % N |
| Calc. | 64.97 | 8.02 | 4.46 |
| Found | 65.12 | 8.16 | 4.44 |

Example 17

Synthesis of (1S,5S,9S)-(+)-2-Isopropyl-2',5,9-trimethyl-6,7-benzomorphan ((+)-BZ-28) and HCl salt thereof ((+)-BZ-28.HCl)

(+)-BZ-22.HCl was prepared in the manner of the synthesis of (+)-IIId-4.HCl (FIG. 2 and 3) using p-methylbenzylmagnesium bromide instead of benzylmagnesium chloride.

Figure 17:
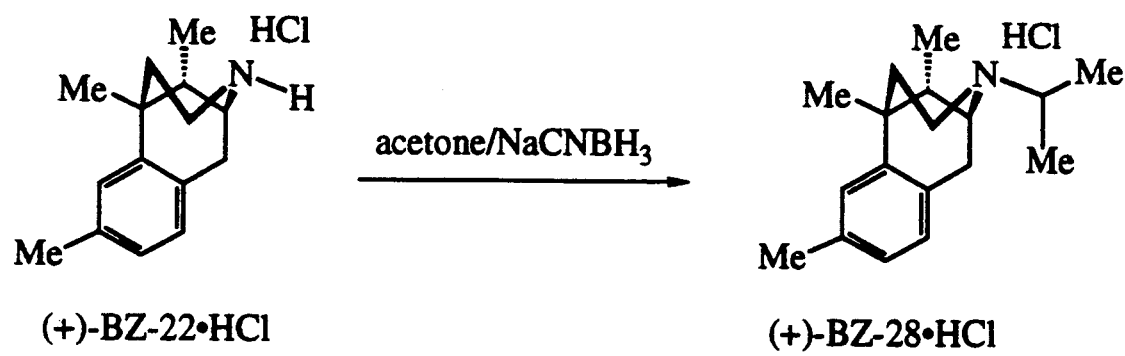
FIG. 17 is a depiction of the chemical reactions employed in Example 17.

As shown in FIG. 17 (Scheme 17), to a solution of 0.228 g of (+)BZ-22.HCl (0.90 mmol) in 15 mL of acetone at reflux was added NaCNBH$_3$ [0.228 g, 3.6 mmol (excess)] with stirring. Then 3N HCl was added dropwise over 1 h until the NaCNBH$_3$ was consumed. After the usual workup, the crude product in ether was filtered through a short silica pad to remove trace polar impurities, and the filtrate was spin-evaporated. Then, the residue was dissolved in 4 mL of $CH_2Cl_2$/ether (1:1), treated with HCl/ether, and white crystals formed. The slurry was then diluted with ether (40 mL), and pure (+)BZ-28.HCl was collected (0.13 g, 49%).

BZ-28.HCl $^1$H NMR ($CDCl_3$, 300 MHz) δ7.1 (brs, 1H, aromatic), 7.0 (m, 2H, aromatic), 3.82 (brs, 1H, $C_1$—H), 3.30 (m, 1H, $C_\alpha$—H), 2.32 (s, 3H, $C_2$, —$CH_3$), 1.60 (2d, 6H, $CH_3$ of i-Pr), 1.46 (s, 3H, $C_5$—$CH_3$), 0.92 (d, 3H, $C_9$—$CH_3$). MS: m/z 257 (parent ion), 242 (M-$CH_3$).

In Vitro Binding Assay at the NMDA Receptor Site, μ-Site and σ-Site of Opioid Receptor Compounds such as MK-801, DAGO and PPP have been shown to be high-affinity ligands at the NMDA receptor site, and the μ site and σ site of the opioid receptor respectively. As described below, the compounds of the invention were tested for their ability to inhibit binding of radiolabeled versions of these known ligands. ($[^3H]$MK-801)

Semipurified synaptic membranes were prepared according to the method of Bristow et al. (1986) with minor modifications. Sprague-Dawley rats were decapitated and the forebrains were removed, weighed, and homogenized in 20 volumes of 0.32M sucrose. The homogenate was centrifuged at $121 \times G$ for 10 min. The resulting supernatant was recentrifuged at $27,000 \times G$ for 15 min. The pellet was resuspended in 20 volumes of distilled water and this suspension was centrifuged at $8,000 \times G$ for 10 min. Both the supernatant and the buffy coat layer, removed with 2 mL of 5 mM Tris-Cl (pH 7.8), were pooled and centrifuged at $27,000 \times G$ for 15 min. The supernatant was removed, the pellet was covered with a small amount of 5 mM Tris-Cl, and the sample was frozen for at least 18 hrs at $-20°$ C. Membranes were then washed four times in 5 mM Tris-Cl and finally resuspended in 25 mL. This preparation was used for the binding assay immediately or frozen for subsequent use.

To maximally stimulate $[^3H]$MK-801 binding, glycine (final concentration 50 μM) and glutamate (50 μM) were added to the membrane preparation. Varying concentrations of the test compounds (100 μL) and $[^3H]$MK-801 (100 μL, final concentration 3 nM) were mixed with 1.3 mL of the membrane preparation and incubated at 37° C. for 2 hours. The incubation was terminated by rapid filtration (Brandel Cell Harvester) over Whatman GF/B filters, which were then washed twice with 5 mL of 5 mM Tris-HCl. Radioactivity trapped on the filters was counted in 5 mL Scintiverse II at 50% efficiency in 7 mL minivials after standing at room temperature overnight. Unlabeled MK-801 (100 μM) was used to estimate nonspecific binding.

($[^3H]$DAGO)

Semipurified synaptic membranes were prepared according to the method of Toll et al. (1984). Adult male Sprague-Dawley rats were decapitated, and the forebrains were removed, weighed, and homogenized in 20 volumes of 50 M Tris-HCl, pH 7.7. The homogenate was centrifuged at $27,000 \times G$ for 15 minutes, and the resulting pellet was resuspended in buffer and recentrifuged twice. The washed membranes were resuspended in buffer to obtain a membrane concentration of 7.2 mg brain weight/mL; the final concentration in each assay tube was 12.2 mg/2 mL. Various concentrations of the test compounds (200 μL) and $[^3H]$DAGO (100 μL, final concentration 2 nM) were incubated with 1.7 mL of the membrane preparation at 25° C. for 1 hour. Unlabeled DAGO (final concentration 10 μM) was added to some tubes to estimate nonspecific binding (about 10% of total binding). The reaction was stopped by filtration through GF/B filters using a Brandel Cell Harvester. After washing twice with 5 mL of ice cold buffer, the filters were suspended in 5 mL scintillation fluid, and the radioactivity was counted after standing at room temperature overnight.

($[^3H]$PPP)

Hartley guinea pigs were decapitated, and the brains were removed and homogenized in 20 volumes of 50 mM Tris-HCl using a Polytron homogenizer. The homogenate was centrifuged at $27,000 \times G$ for 15 minutes, and the pellet was resuspended in 50 mM Tris-HCl. The centrifugation procedure was repeated twice. The pellet was diluted to approximately 8 mg wet tissue/assay. Various concentrations of the test compounds (100 μL) and $[^3H]$PPP (100 μL, final concentration 0.6 nM) were incubated with 1.8 mL of the tissue homogenate at 25° C. for 1 hour. Unlabeled PPP (final concentration 10 μM) was added to some tubes to determine nonspecific binding. The reaction was stopped by filtration through GF/B filters using a Brandel Cell Harvester. After washing twice with 50 mM of ice cold Tris-HCl, the filters were suspended in 5 mL of scintillation fluid, and the radioactivity was counted after standing at room temperature overnight.

Table 1 summarizes the results of the in vitro binding studies using these three radioligands at the NMDA receptor site, μ-site and σ-site of opioid receptor, respectively.

$K_i$ values were calculated from the following equation:

$$Ki = \frac{IC_{50}}{1 + \frac{[c]}{Kd}}$$

where $K_d$ values for $[^3H]$MK-801, $[^3H]$DAGO and $[^3H]$PPP are 5.6 nM, 2.0 nM and 20 nM, respectively.

In Vivo Protection in the Mouse Against NMDA-Induced Lethality

According to the method described by Ferkany et al. (1988), the test compounds were administered ip to four male Swiss-Webster mice (26-34 g) each, following 30 minutes later, 200 mg/kg of NMDA was administered to the mice each. The $LD_{50}$ of NMDA was found to be 164 mg/kg, and approximately 90% of the mice died at 200 mg/kg. Those compounds that protected three or more of the mice at any of the doses were evaluated further by determining the $ED_{50}$ values using three or more doses with the eight mice per dose. The $ED_{50}$ was estimated by the method of Litchfield and Wilcoxin (1949). Water-soluble compounds were dissolved in distilled water and administered in a volume of 10 ml/kg. Water-insoluble compounds were suspended in an aqueous solution of 0.5% methyl cellulose and administered in a volume of 20 ml/kg.

Table 1 also summarizes the results of this test.

TABLE 1

| Compound | | K_i(μM) [³H]MK801 | [³H]DAGO | [³H]PPP | Mouse ED₅₀ |
|---|---|---|---|---|---|
| Dextromethorphan | | 2.75 | 1.74 | 0.15 | 39.0 |
| Dextrorphan | | 0.52 | 2.2 | — | 34.6 |
| (+)-IIId-6 | [Example 3] | 3.51 | 18.9 | 0.56 | 17.3 |
| (+)-IIId-7 (Isomer A) | [Example 4] | 0.75 | 3.05 | 0.020 | 6.8 |
| (+)-IIId-7 (Isomer B) | [Example 4] | 1.99 | 6.58 | 0.071 | 13.7 |
| (+)-BZ-1 | [Example 5] | 14.0 | 11.5 | 0.16 | 33.1 |
| (+)-BZ-2 | [Example 6] | 1.32 | 9.58 | 0.10 | 22.1 |
| (+)-BZ-3 (Isomer A) | [Example 7] | 0.22 | 11.80 | 0.0012 | 16.4 |
| (+)-BZ-3 (Isomer B) | [Example 7] | 3.61 | 13.53 | 0.0081 | >60.0 |
| (+)-BZ-4 | [Example 8] | 11.51 | 20.21 | 0.13 | 24.1 |
| (+)-BZ-6 (Isomer A) | [Example 9] | 16.56 | 12.3 | 19.2 | >50.0 |
| (+)-BZ-6 (Isomer B) | [Example 9] | 2.55 | 9.00 | 1.10 | 18.8 |
| (+)-BZ-5 | [Example 10] | 11.6 | 5.8 | 0.011 | — |
| (+)-BZ-5 (Isomer A) | [Example 10] | 29.18 | 9.74 | 0.040 | — |
| (+)-BZ-5 (Mixture of Isomer B and C) | [Example 10] | — | 12.4 | 0.042 | 32.5 |
| (+)-BZ-13 | [Example 11] | 4.15 | 20.20 | 0.26 | 9.0 |
| (+)-BZ-14 (Isomer A) | [Example 12] | 0.85 | 0.72 | 0.014 | 6.1 |
| (+)-BZ-14 (Isomer B) | [Example 12] | 3.53 | 5.01 | 0.062 | 13.0 |
| (+)-BZ-15A | [Example 13] | 2.59 | 7.29 | 0.98 | 10.7 |
| (+)-BZ-17A | [Example 14] | 42.98 | 21.89 | 25.95 | 21.6 |
| (+)-BZ-18 | [Example 15] | 4.54 | — | 0.81 | 14.4 |
| (+)-BZ-26 | [Example 16] | 12.80 | 11.75 | 0.074 | 12.2 |

Representative pharmaceutical compositions can be formed as follows:

| Representative Composition A An oral suspension is prepared having the following composition: | |
|---|---|
| Ingredients | |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

| Representative Composition B | |
|---|---|
| Ingredients | Quantity per tablet (mg) |
| active ingredient | 25 |
| cornstarch | 20 |
| lactose, spray-dried | 153 |
| magnesium stearate | 2 |

The above ingredients are thoroughly mixed and pressed into single-scored tablets.

| Representative Composition C | |
|---|---|
| Ingredients | |
| active ingredient | 25 mg |
| injectable saline | 1 mL |

These materials are mixed to give an injectable solution/suspension.

What is claimed is:

1. A compound of the formula

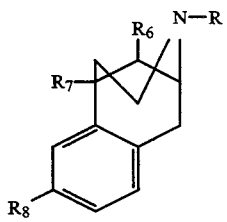

or a pharmaceutically acceptable salt thereof, wherein
R is —CR₁R₂R₃, in which
R₁ is hydrogen,
R₂ is an alkyl group having 1 to 4 carbon atoms, and
R₃ is a cycloalkyl group having 3 to 7 carbon atoms;
R₆ and R₇ are each independently hydrogen or an alkyl group having 1 to 4 carbon atoms; and
R₈ is hydrogen.

2. The compound or pharmaceutically acceptable salt of claim 1 wherein R₂ is methyl.

3. The compound or pharmaceutically acceptable salt of claim 1 wherein R₃ is cyclopropyl.

4. The compound or pharmaceutically acceptable salt of claim 1 wherein R₃ is cyclobutyl.

5. The compound or pharmaceutically acceptable salt of claim 1 wherein R₆ is methyl and R₇ is methyl.

6. The compound or pharmaceutically acceptable salt of claim 1 in substantially optically pure (+)-isomer form.

7. A pharmaceutical composition comprising an effective amount of the compound or pharmaceutically acceptable salt of claim 1 in combination with a pharmaceutically acceptable carrier.

8. 2-(1-cyclopropylethyl)-5,9-dimethyl-6,7-benzomorphan or a pharmaceutically acceptable salt thereof.

9. 2-(1-cyclopropylethyl)-5,9-dimethyl-6,7-benzomorphan or a pharmaceutically acceptable salt thereof.

10. (+)-2-(1-cyclopropylethyl)-5,9-dimethyl-6,7-benzomorphan or a pharmaceutically acceptable salt thereof.

11. (+)-2-(1-cyclobutylethyl)-5,9-dimethyl-6,7-benzomorphan or a pharmaceutically acceptable salt thereof.

12. (1S,5S,9S)-(+)-2-(1-cyclopropylethyl)-5,9-dimethyl-6,7-benzomorphan or a pharmaceutically acceptable salt thereof.

13. (1S,5S,9S)-(+)-2-(1-cyclobutylethyl)-5,9-dimethyl-6,7-benzomorphan or a pharmaceutically acceptable salt thereof.

14. Isomer A of (1S,5S,9S)-(+)-2-(1-cyclopropylethyl)-5,9-dimethyl-6,7-benzomorphan or a pharmaceutically acceptable salt thereof.

15. Isomer A of (1S,5S,9S)-(+)-2-(1-cyclobutylethyl)-5,9-dimethyl-6,7-benzomorphan or a pharmaceutically acceptable salt thereof.

* * * * *